(12) United States Patent
Bergersen

(10) Patent No.: US 10,524,742 B2
(45) Date of Patent: Jan. 7, 2020

(54) SYSTEM AND METHOD FOR DETERMINING AN ORTHODONTIC DIAGNOSTIC ANALYSIS OF A PATIENT

(71) Applicant: Ortho-Tain, Inc., Winnetka, IL (US)

(72) Inventor: Earl O. Bergersen, Dorado, PR (US)

(73) Assignee: Ortho-Tain, Inc.

( * ) Notice: Subject to any disclaimer, the term of this patent is extended or adjusted under 35 U.S.C. 154(b) by 128 days.

(21) Appl. No.: 15/619,700

(22) Filed: Jun. 12, 2017

(65) Prior Publication Data

US 2017/0273646 A1    Sep. 28, 2017

Related U.S. Application Data

(63) Continuation of application No. 14/294,404, filed on Jun. 3, 2014, now Pat. No. 9,675,305.

(51) Int. Cl.
| | |
|---|---|
| *G06K 9/00* | (2006.01) |
| *A61B 6/14* | (2006.01) |
| *A61C 7/00* | (2006.01) |
| *G16H 20/00* | (2018.01) |
| *G16H 50/70* | (2018.01) |
| *G16H 30/40* | (2018.01) |

(52) U.S. Cl.
CPC ............... *A61B 6/14* (2013.01); *A61C 7/002* (2013.01); *G16H 20/00* (2018.01); *G16H 30/40* (2018.01); *G16H 50/70* (2018.01)

(58) Field of Classification Search
CPC combination set(s) only.
See application file for complete search history.

(56) References Cited

U.S. PATENT DOCUMENTS

| | | | |
|---|---|---|---|
| 5,278,756 | A | 1/1994 | Lemchen et al. |
| 5,453,009 | A | 9/1995 | Feldman |
| 5,458,487 | A | 10/1995 | Komatsu et al. |
| 5,683,243 | A | 11/1997 | Andreiko et al. |
| 5,882,192 | A | 3/1999 | Bergersen |
| 6,089,868 | A | 7/2000 | Jordan et al. |
| 6,099,314 | A | 8/2000 | Kopelman et al. |
| 6,217,325 | B1 | 4/2001 | Chishti et al. |
| 6,217,334 | B1 | 4/2001 | Hultgren |
| 6,227,850 | B1 | 5/2001 | Chishti et al. |
| 6,582,225 | B1 | 6/2003 | Bergersen |

(Continued)

OTHER PUBLICATIONS

European Patent Office; Extended European Search Report issued in Application No. 15170212.3; dated Oct. 29, 2015, 5 pages.

*Primary Examiner* — Alex Kok S Liew
(74) *Attorney, Agent, or Firm* — Taft Stettinius & Hollister

(57) ABSTRACT

A method including the steps of: providing a plurality of diagnostic programs associated with characteristics of developing dentition of a patient; performing an initial assessment of the patient corresponding to the developing dentition of the patient wherein the initial assessment uses an imaging device to locate points in a mouth of the patient wherein the imaging device generates imaging data; transferring the imaging data to a central processing unit wherein the central processing unit obtains measurements associated with selected points in the mouth of the patient and predicts future orthodontic conditions of the patient based upon the measurements; and providing a report of findings of the initial assessment to the patient with treatment recommendations based upon the findings.

19 Claims, 21 Drawing Sheets

(56) References Cited

U.S. PATENT DOCUMENTS

| | | |
|---|---|---|
| 8,303,301 B2 | 11/2012 | Bergersen |
| 2003/0215764 A1 | 11/2003 | Kopelman et al. |
| 2003/0224312 A1 | 12/2003 | Bergersen |
| 2004/0197727 A1* | 10/2004 | Sachdeva ................ A61C 7/00 433/24 |
| 2005/0010450 A1* | 1/2005 | Hultgren ............ A61C 13/0004 705/3 |
| 2005/0089214 A1* | 4/2005 | Rubbert .................. A61C 7/00 382/154 |
| 2006/0269896 A1 | 11/2006 | Liu et al. |
| 2006/0275736 A1 | 12/2006 | Wen et al. |
| 2007/0141527 A1 | 6/2007 | Kuo et al. |
| 2007/0244718 A1 | 10/2007 | Arnone et al. |
| 2010/0114080 A1* | 5/2010 | Theriault ............... A61B 18/20 606/9 |
| 2010/0170052 A1 | 7/2010 | Ortins et al. |
| 2011/0293156 A1 | 12/2011 | Hsiao et al. |

* cited by examiner

| Symptom of patient | Appliance most applicable | Recommended Uses |
|---|---|---|
| -open bite<br>-overjet or no overjet<br>-mouth breather<br>-narrow palate<br>  3-4 mm narrow | Habit corrector #1<br>With occlusal pads for open bite open version initially | Use Habit Corrector #1 day (2 hours passively) and at night with lateral tongue pressure. Then begin using Habit Corrector #2 during the day and Habit Corrector #1 at night |
| -sucks thumb<br>-speech problem<br>-sleep problem<br>-snoring | Habit Corrector #2<br>Same appliance but closed version | After two weeks longer, use Habit Corrector #2 all the time. Two hours passively during the day and all night. Continue every night for sleep problems. |
| -normal overbite<br>- (1mm) overjet<br>-mouth breath at night<br>-narrow palate<br>  3-4 mm narrow<br>-sucks thumb<br>-speech problem<br>-sleep problem<br>-snoring | Habit Corrector #2 | Use two hours passively in the day with lateral tongue action, and at night. Use nightly for sleep and snoring problems. |
| -overbite 1, 2, 5mm<br>-overjet or no overjet<br>-other malocclusion problem<br>-sleep and snoring problem<br>pseudo class III | Nite-Guide® | Wear only at night & continue for sleep and snoring problems. |
| -pseudo class III<br>-skeletal class III<br>  (up to 3 mm severity)<br>-no sleep problem<br>-no snoring problem | Youth Class III Appliance | Wear 2 hours during the day and push tongue forward against pre maxilla |

FIG. 5

| Symptom and amount | Incidence | % Risk of patient at 12 yrs of age | Predicted severity of problem by 12 yrs of age | Treatment Recommendation |
|---|---|---|---|---|
| Crowding 2 mm | 13.0% | 100% | Crowding 4.8 mm | Strongly recommend |
| Overbite (vertical overlap) 4.5 mm | 5.6% | 100% | Overbite 8.7 mm | Strongly recommend |
| Overjet (horizontal distance) 2.0 mm | 37.1% | 23.1% | Overjet 1.8 mm | Not recommend |
| Cross-bite none | 16.0% | 45% | Cross-bite 7.2% | Not recommend |
| TMJ problems present | 21.1% | 100% | 39.9% | Strongly recommend |
| Habits daytime mouth breather | 25.6% | 100% | same | Strongly recommend |
| Sleep/Breathing problems none | 61.1% | 0% | 0% | Not recommended |
| Arch width normal | 92.5% | 0% | 0% | Not recommended |

FIG. 6

| SA 14-0 | 8-0 | 8-6 | 9-0 | 9-6 | 10-0 | 10-6 | 11-0 | 11-6 | 12-0 | 12-6 | 13-0 | 13-6 |
|---|---|---|---|---|---|---|---|---|---|---|---|---|
| Rate of Prediction | | | | | | | | | | | | |
| 67% | ±7 mo. | 7 mo. | 7 mo. | 6 mo. | 7 mo. | 6 mo. | 6 mo. | 5 mo. | 6 mo. | 5 mo. | 5 mo. | 5 mo. |
| 95% | ±15 mo. | 13 mo. | 14 mo. | 13 mo. | 13 mo. | 12 mo. | 11 mo. | 11 mo. | 12 mo. | 10 mo. | 9 mo. | 10 mo. |

| CA | | | | | | | | | | | | | |
|---|---|---|---|---|---|---|---|---|---|---|---|---|---|
| 6-0 | 8-9 | | | | | | | | | | | | |
| 6-3 | 9-0 | | | | | | | | | | | | |
| 6-6 | 9-3 | 8-9 | | | | | | | | | | | |
| 6-9 | 9-6 | 9-1 | | | | | | | | | | | |
| 7-0 | 9-10 | 9-4 | 8-9 | | | | | | | | | | |
| 7-3 | 10-1 | 9-7 | 9-0 | | | | | | | | | | |
| 7-6 | 10-4 | 9-10 | 9-4 | 8-7 | | | | | | | | | |
| 7-9 | 10-7 | 10-2 | 9-7 | 8-11 | | | | | | | | | |
| 8-0 | 10-10 | 10-5 | 9-10 | 9-2 | 8-10 | | | | | | | | |
| 8-3 | 11-2 | 10-8 | 10-2 | 9-6 | 9-1 | | | | | | | | |
| 8-6 | 11-5 | 10-11 | 10-5 | 9-10 | 9-5 | 8-10 | | | | | | | |
| 8-9 | 11-8 | 11-2 | 10-8 | 10-1 | 9-8 | 9-1 | | | | | | | |
| 9-0 | 11-11 | 11-6 | 11-0 | 10-5 | 9-11 | 9-5 | 8-11 | | | | | | |
| 9-3 | 12-3 | 11-9 | 11-3 | 10-8 | 10-3 | 9-8 | 9-2 | | | | | | |
| 9-6 | 12-6 | 12-0 | 11-6 | 11-0 | 10-6 | 10-0 | 9-5 | 8-10 | | | | | |
| 9-9 | 12-9 | 12-3 | 11-10 | 11-4 | 10-10 | 10-3 | 9-9 | 9-1 | | | | | |
| 10-0 | 13-0 | 12-6 | 12-1 | 11-7 | 11-1 | 10-7 | 10-0 | 9-5 | 8-11 | | | | |
| 10-3 | 13-3 | 12-10 | 12-4 | 11-11 | 11-5 | 10-10 | 10-4 | 9-8 | 9-3 | | | | |
| 10-6 | 13-7 | 13-1 | 12-8 | 12-3 | 11-8 | 11-2 | 10-7 | 10-0 | 9-6 | 8-10 | | | |
| 10-9 | 13-10 | 13-4 | 12-11 | 12-6 | 11-11 | 11-6 | 10-11 | 10-3 | 9-9 | 9-1 | | | |
| 11-0 | 14-1 | 13-7 | 13-3 | 12-10 | 12-3 | 11-9 | 11-2 | 10-7 | 10-1 | 9-4 | 8-10 | | |
| 11-3 | 14-4 | 13-10 | 13-6 | 13-2 | 12-6 | 12-1 | 11-5 | 10-11 | 10-4 | 9-8 | 9-1 | | |
| 11-6 | | 14-2 | 13-9 | 13-5 | 12-10 | 12-4 | 11-9 | 11-2 | 10-7 | 9-11 | 9-5 | 8-11 | |
| 11-9 | | 14-5 | 14-1 | 13-9 | 13-1 | 12-8 | 12-1 | 11-6 | 10-11 | 10-3 | 9-8 | 9-2 | |
| 12-0 | | | 14-4 | 14-0 | 13-5 | 12-11 | 12-4 | 11-9 | 11-2 | 10-6 | 9-11 | 9-5 | 9-1 |
| 12-3 | | | 14-7 | 14-4 | 13-8 | 13-3 | 12-8 | 12-1 | 11-5 | 10-9 | 10-3 | 9-9 | 9-4 |
| 12-6 | | | | 14-8 | 14-0 | 13-7 | 12-11 | 12-4 | 11-9 | 11-1 | 10-6 | 10-0 | 9-7 |
| 12-9 | | | | 14-11 | 14-3 | 13-10 | 13-3 | 12-8 | 12-0 | 11-4 | 10-10 | 10-3 | 9-10 |
| 13-0 | | | | | 14-6 | 14-2 | 13-6 | 13-0 | 12-3 | 11-8 | 11-1 | 10-7 | 10-2 |
| 13-3 | | | | | 14-10 | 14-5 | 13-10 | 13-3 | 12-7 | 11-11 | 11-4 | 10-10 | 10-5 |
| 13-6 | | | | | | 14-9 | 14-1 | 13-7 | 12-10 | 12-2 | 11-8 | 11-2 | 10-8 |
| 13-9 | | | | | | 15-0 | 14-4 | 13-10 | 13-1 | 12-6 | 11-11 | 11-5 | 10-11 |
| 14-0 | | | | | | | 14-8 | 14-2 | 13-5 | 12-9 | 12-2 | 11-8 | 11-3 |
| 14-3 | | | | | | | 14-11 | 14-5 | 13-8 | 13-1 | 12-6 | 12-0 | 11-6 |
| 14-6 | | | | | | | | 14-9 | 13-11 | 13-4 | 12-9 | 12-3 | 11-9 |
| 14-9 | | | | | | | | 15-1 | 14-3 | 13-8 | 13-0 | 12-6 | 12-0 |
| 15-0 | | | | | | | | | 14-6 | 13-11 | 13-4 | 12-10 | 12-3 |
| 15-3 | | | | | | | | | 14-9 | 14-2 | 13-7 | 13-1 | 12-7 |
| 15-6 | | | | | | | | | | 14-6 | 13-10 | 13-4 | 12-10 |
| 15-9 | | | | | | | | | | 14-9 | 14-2 | 13-8 | 13-1 |
| 16-0 | | | | | | | | | | | 14-5 | 13-11 | 13-4 |
| 16-3 | | | | | | | | | | | 14-8 | 14-3 | 13-8 |
| 16-6 | | | | | | | | | | | | 14-6 | 13-11 |
| 16-9 | | | | | | | | | | | | 14-9 | 14-2 |
| 17-0 | | | | | | | | | | | | | 14-5 |
| 17-3 | | | | | | | | | | | | | 14-9 |

FIG. 7

| Males | | | Females | | |
|---|---|---|---|---|---|
| Age | ANS-Me Growth Remaining | Successful Overbite Correction Possible | Age | ANS-Me Growth Remaining | Successful Overbite Correction Possible |
| 6 yrs | 12.5 mm | 13.5 mm | 6 yrs | 8.1 mm | 9.1 mm |
| 7 yrs | 11.4 mm | 12.4 mm | 7 yrs | 7.2 mm | 8.2 mm |
| 8 yrs | 10.6 mm | 11.6 mm | 8 yrs | 6.6 mm | 7.6 mm |
| 9 yrs | 9.8 mm | 10.8 mm | 9 yrs | 5.8 mm | 6.8 mm |
| 10 yrs | 8.8 mm | 9.8 mm | 10 yrs | 5.1 mm | 6.1 mm |
| 11 yrs | 7.8 mm | 8.8 mm | 11 yrs | 4.3 mm | 5.3 mm |
| 12 yrs | 6.9 mm | 7.9 mm | 12 yrs | 3.3 mm | 4.3 mm |
| 13 yrs | 5.8 mm | 6.8 mm | 13 yrs | 2.5 mm | 3.5 mm |
| 14 yrs | 4.4 mm | 5.4 mm | 14 yrs | 1.7 mm | 2.7 mm |
| 15 yrs | 2.7 mm | 3.7 mm | 15 yrs | 1.2 mm | 2.2 mm |
| 16 yrs | 1.5 mm | 2.5 mm | 16 yrs | 0.8 mm | 1.8 mm |
| 17 yrs | 0.7 mm | 1.8 mm | 17 yrs | 0.6 mm | 1.6 mm |
| 18 yrs | 0 mm | 1.0 mm | 18 yrs | 0 mm | 1.0 mm |

FIG. 8

| Males | | | Females | | |
|---|---|---|---|---|---|
| Age | ART-GN Growth Remaining | Successful Overjet Correction Possible | Age | ART-GN Growth Remaining | Successful Overjet Correction Possible |
| 6 yrs | 26.4 mm | 27.4 mm | 6 yrs | 18.9 mm | 19.9 mm |
| 7 yrs | 23.8 mm | 24.8 mm | 7 yrs | 16.4 mm | 17.4 mm |
| 8 yrs | 21.5 mm | 22.5 mm | 8 yrs | 14.3 mm | 15.3 mm |
| 9 yrs | 19.5 mm | 20.5 mm | 9 yrs | 12.8 mm | 13.8 mm |
| 10 yrs | 17.4 mm | 18.4 mm | 10 yrs | 10.9 mm | 11.9 mm |
| 11 yrs | 15.5 mm | 16.5 mm | 11 yrs | 8.6 mm | 9.6 mm |
| 12 yrs | 13.6 mm | 14.6 mm | 12 yrs | 6.2 mm | 7.2 mm |
| 13 yrs | 11.6 mm | 12.6 mm | 13 yrs | 4.4 mm | 5.4 mm |
| 14 yrs | 9.0 mm | 10.0 mm | 14 yrs | 2.6 mm | 3.6 mm |
| 15 yrs | 6.0 mm | 7.0 mm | 15 yrs | 1.5 mm | 2.5 mm |
| 16 yrs | 3.6 mm | 4.6 mm | 16 yrs | 0.9 mm | 1.9 mm |
| 17 yrs | 1.9 mm | 2.9 mm | 17 yrs | 0.6 mm | 1.6 mm |
| 18 yrs | 0 mm | 1.0 mm | 18 yrs | 0 mm | 1.0 mm |

FIG. 9

| Symptom | Acceptable normal amount | Incidence | Risk of problems by 12 years of age | Resultant problem by 12 years of age | Treatment recommendation |
|---|---|---|---|---|---|
| Snores habitually 5-7 nights per week | 0 Or snores only very infrequently | 3.5% | Serious risk For cardio-vascular or cardio respiratory problems | Significant problem | Strongly recommend |
| Hyperactive | Moderately present in 21.1% | Habitual snorers 58.8% Occasional snorers 84.0% | Problem does not improve with age | Probably significant problem | Strongly recommend |
| Attention deficit | Moderately present in 11.1% Especially boys | Habitual snorers 31.9% Occasional snorers 18.0% | Strong risk | Probably significant problem | Strongly recommend |
| Daytime mouth breathing | Moderately present in 18.4% | Habitual snorers 65.9% Occasional snorers 34.0% | Strong risk | Probably significant problem | Strongly recommend |

FIG. 11

| Patient's overjet | Normal acceptable amount | Incidence % | Risk of problem over 3mm by 12 yrs of age | Projected overjet by 12 yrs of age | Treatment Recommendations |
|---|---|---|---|---|---|
| 1 mm | 1 to less than 3mm | 52.8% | 71.1% | 2.4 mm | Not recommended |
| 2 mm | 1 to less than 3mm | 16.7% | 83.3% | 3.3 mm | Optionally recommended unless have sleep problems |
| 3 mm | 1 to less than 3mm | 11.1% | 88.7% | 4.7 mm | Strongly recommended |
| 4-6 mm | 1 to less than 3mm | 8.3% | 94.3% | 3.6 mm | Strongly recommended |
| 7-8 mm | 1 to less than 3mm | 5.6% | 100% | 3.9 mm | Strongly recommended |

FIG. 12

| Crowding/spacing at 7 yrs | Incidence | Risk of problem at 12 yrs of age | Projected amount by 12 yrs | Treatment Recommendation |
|---|---|---|---|---|
| -8 mm & over crowding | 6.3% | 100% | -6.7 mm crowding | Strongly recommend |
| -6 mm & -7 mm crowding | 10.4% | 100% | -4.1 mm crowding | Strongly recommend |
| -5 mm crowding | 10.4% | 100% | -8.0 mm crowding | Strongly recommend |
| -4 mm crowding | 8.3% | 100% | -5.0 mm crowding | Strongly recommend |
| -3 mm crowding | 6.3% | 100% | -3.5 mm crowding | Strongly recommend |
| -2 mm crowding | 22.9% | 90.9% | -3.5 mm crowding | Strongly recommend |
| -1 mm crowding | 8.3% | 75% | -1.9 mm crowding | Strongly recommend |
| 0 no crowding no spacing | 20.8% | 90% | -2.1 mm crowding | Strongly recommend |
| +1 mm spacing | 2.1% | 100% | -1.7 mm crowding | Strongly recommend |
| +2 mm spacing | 4.2% | 0% | +1.3 mm spacing | Do not recommend |
| +3 mm & over spacing | 6.3% | 0.0% | +3.5 mm spacing | Optionally recommend for space closure |

FIG. 13

| Overbite present | Incidence | % Risk of Overbite ≥ 1mm by 12 yrs of age | Prediction of overbite by 12 yrs of age | Treatment Recommendations |
|---|---|---|---|---|
| 5 mm overbite | 8.3% | 100% | 6.2 mm | Strongly recommend |
| 4 mm overbite | 2.8% | 100% | 5.0 mm | Strongly recommend |
| 3 mm overbite | 22.2% | 100% | 5.2 mm | Strongly recommend |
| 2 mm overbite | 19.4% | 100% | 4.2 mm | Strongly recommend |
| 1 mm overbite | 13.9% | 87.5% | 3.2 mm | Strongly recommend |
| 0 mm overbite edge to edge | 19.4% | 85.7% | 2.4 mm | Strongly recommend |
| -1mm open bite | 11.1% | 75% | 2.4 mm | Optionally recommend, see at 10 yrs of age. |

FIG. 14

| Overjet Present | Incidence | Risk of excess overjet by 12 yrs of age | Prediction of overjet by 12 yrs of age | Treatment Recommendations |
|---|---|---|---|---|
| 6 mm overjet | 2.8% | 100% | 6.7 mm | Strongly Recommend |
| 5 mm overjet | 2.8% | 100% | 4.9 mm | Strongly Recommend |
| 4 mm overjet | 13.9% | 100% | 3.5 mm | Strongly Recommend |
| 3 mm overjet | 11.1% | 100% | 4.1 mm | Strongly Recommend |
| 2 mm overjet | 22.2% | 100% | 2.6 mm | Strongly Recommend |
| 1 mm overjet normal | 30.6% | 100% | 2.6 mm | Strongly Recommend |
| 0 mm end to end | 16.7% | 100% | 2.3 mm | Strongly Recommend |

FIG. 15

| Patient's Overbite | Length of Treatment M & F | Recommended Retention M & F | Patient's Overjet | Length of Treatment M & F | Recommended Retention M & F |
|---|---|---|---|---|---|
| 2 mm | 2-4 months | M  1 year<br>F  1 year 5 mos. | 2 mm | 2-4 months | M  3 mos.<br>F  4 mos. |
| 3 mm | 3-5 months | M  1 year 10 mos.<br>F  2 years 9 mos. | 3 mm | 3-5 months | M  8 mos.<br>F  9 mos. |
| 4 mm | 4-6 months | M  2 years 11 mos.<br>F  4 years 0 mos. | 4 mm | 4-6 months | M  1 year 1 mo.<br>F  1 year 4 mos. |
| 5 mm | 5-7 months | M  3 years 10 mos.<br>F  4 years 10 mos. | 5 mm | 5-7 months | M  1 year 5 mos.<br>F  1 year 9 mos. |
| 6 mm | 6-8 months | M  4 years 5 mos.<br>F  6 years 0 mos. | 6 mm | 6-8 months | M  1 years 10 mos.<br>F  2 years 1 mos. |
| 7 mm | 7-9 months | M  6 years 6 mos.<br>F  7 years 0 mos. | 7 mm | 7-9 months | M  2 years 3 mos.<br>F  2 years 6 mos. |
| | | | 8 mm | 8-10 months | M  2 years 8 mos.<br>F  2 years 11 mos. |
| | | | 9 mm | 9-11 month | M  3 years 1 mos.<br>F  3 years 2 mos. |
| | | | 10 mm | 10-12 months | M  3 years 7 mos.<br>F  3 years 7 mos. |
| | | | 11 mm | 11-13 months | M  4 years<br>F  4 years |
| | | | 12 mm | 12-14 months | M  4 years 5 mos.<br>F  5 years 7 mos. |

FIG. 16

| a | b | c | d | e | f |
|---|---|---|---|---|---|
| Age of Patient Male | Maximum amount of overbite with minimal relapse | ANS-ME growth remaining | Overbite correction available with minimal relapse | Amount of Overbite that will result in Relapse | Expected Relapse |
| 7 yrs | 12.4 mm | 11.4 mm | 11.4 mm | >12.4 mm | Overbite >12.4 mm expect relapse |
| 8 yrs | 11.6 mm | 10.6 mm | 10.6 mm | >11.6 mm | Overbite >11.6 mm expect relapse |
| 9 yrs | 10.8 mm | 9.8 mm | 9.8 mm | >10.8 mm | Overbite >10.9 mm expect relapse |
| 10 yrs | 9.8 mm | 8.8 mm | 8.8 mm | >9.8 mm | Overbite >9.8 mm expect relapse |
| 11 yrs | 8.8 mm | 7.8 mm | 7.8 mm | >8.8 mm | Overbite >8.8 mm expect relapse |
| 12 yrs | 7.9 mm | 6.9 mm | 6.9 mm | >7.9 mm | Overbite >7.9 mm expect relapse |
| 13 yrs | 6.8 mm | 5.8 mm | 5.8 mm | >6.8 mm | Overbite >6.8 mm expect relapse |
| 14 yrs | 5.4 mm | 4.4 mm | 4.4 mm | >5.4 mm | Overbite >5.4 mm expect relapse |
| 15 yrs | 3.7 mm | 2.7 mm | 2.7 mm | >3.7 mm | Overbite >3.7 mm expect relapse |
| 16 yrs | 2.4 mm | 1.4 mm | 1.4 mm | >2.4 mm | Overbite >2.4 mm expect relapse |
| 17 yrs | 1.7 mm | 0.7 mm | 0.7 mm | >1.7 mm | Overbite >1.7 mm expect relapse |
| 18 yrs | 1.0 mm | 0 mm | 0 mm | >1.0 mm | Overbite >1.0 mm expect relapse |

FIG. 17

| a | b | c | d | e | f |
|---|---|---|---|---|---|
| Age of Patient Female | Maximum Amount of Overbite with Minimal Relapse | ANS-ME Growth Remaining | Overbite Correction Available with Minimal Relapse | Amount of Overbite that will Result in Relapse | Expected Relapse |
| 7 yrs | 8.2 mm | 7.2 mm | 7.2 mm | >8.2 mm | Overbite > 8.2 mm expect relapse |
| 8 yrs | 7.6 mm | 6.6 mm | 6.6 mm | >7.6 mm | Overbite > 7.6 mm expect relapse |
| 9 yrs | 6.8 mm | 5.8 mm | 5.8 mm | >6.8 mm | Overbite > 6.8 mm expect relapse |
| 10 yrs | 6.1 mm | 5.1 mm | 5.1 mm | >6.1 mm | Overbite > 6.1 mm expect relapse |
| 11 yrs | 5.3 mm | 4.3 mm | 4.3 mm | >5.3 mm | Overbite > 5.3 mm expect relapse |
| 12 yrs | 4.3 mm | 3.3 mm | 3.3 mm | >4.3 mm | Overbite > 4.3 mm expect relapse |
| 13 yrs | 3.5 mm | 2.5 mm | 2.5 mm | >3.5 mm | Overbite > 3.5 mm expect relapse |
| 14 yrs | 2.7 mm | 1.7 mm | 1.7 mm | >2.7 mm | Overbite > 2.7 mm expect relapse |
| 15 yrs | 2.2 mm | 1.2 mm | 1.2 mm | >2.2 mm | Overbite > 2.2 mm expect relapse |
| 16 yrs | 1.8 mm | 0.8 mm | 0.8 mm | >1.8 mm | Overbite > 1.8 mm expect relapse |
| 17 yrs | 1.6 mm | 0.6 mm | 0.6 mm | >1.6 mm | Overbite > 1.6 mm expect relapse |
| 18 yrs | 1.0 mm | 0 mm | 0 mm | >1.0 mm | Overbite > 1.0 mm expect relapse |

FIG. 18

| Crowding/spacing at 12 yrs of age | Incidence | Risk of problem at 18 yrs of age | Projected amount by 18 yrs | Treatment Recommendation |
|---|---|---|---|---|
| -8 mm & over crowding | 7.0% | 100% | -10 mm crowding | Strongly recommend |
| -6 mm & -7 mm crowding | 13.9% | 100% | -5.9 mm crowding | Strongly recommend |
| -5 mm crowding | 7.0% | 100% | -6.7 mm crowding | Strongly recommend |
| -4 mm crowding | 9.3% | 100% | -4.9 mm crowding | Strongly recommend |
| -3 mm crowding | 20.9% | 100% | -3.4 mm crowding | Strongly recommend |
| -2 mm crowding | 9.3% | 100% | -2.6 mm crowding | Strongly recommend |
| -1 mm crowding | 11.6% | 100% | -2.4 mm crowding | Strongly recommend |
| 0 no crowding no spacing | 9.30% | 75% | -0.5 mm crowding | Optionally recommend |
| +1 mm spacing | 4.60% | 0% | +1.3 mm spacing | Do not recommend |
| +2 mm spacing | 4.60% | 0% | +1.3 mm spacing | Do not recommend |
| +3 mm & over spacing | 2.30% | 0% | +3.5 mm spacing | Strongly recommend |

FIG. 19

| Current Overbite mm | Incidence | Risk of problem at 18 yrs of age | Projected overbite by 18 yrs of age | Treatment Recommendation |
|---|---|---|---|---|
| 0 - 1 mm | 5.6% | 0% | 0.6 mm | Do not recommend |
| 1 - <2 mm | 5.6% | 0% | 2.0 mm | Do not recommend |
| 2 - <3 mm | 13.9% | 20% | 1.8 mm | Do not recommend |
| 3 - <4 mm | 13.9% | 80% | 3.2 mm | Strongly recommend |
| 4 - <5 mm | 36.1% | 69.2% | 3.6 mm | Strongly recommend |
| 5 - <6 mm | 13.9% | 100% | 4.3 mm | Strongly recommend |
| 6 - ≤7 mm | 11.1% | 100% | 5.8 mm | Strongly recommend |

FIG. 20

| Patient Current Overjet | Incidence | Risk of excess overjet by 18 yrs | Projected overjet by 18 yrs of age | Treatment Recommendations |
|---|---|---|---|---|
| 6-7 mm overjet and above | 2.8% | 100% | 7.3 mm | Strongly recommend |
| 5 mm overjet | 2.8% | 100% | 3.7 mm | Strongly recommend |
| 4 mm overjet | 5.6% | 100% | 2.7 mm | Strongly recommend |
| 3 mm overjet | 36.1% | 100% | 2.7 mm | Strongly recommend |
| 2 mm overjet | 33.3% | 58.3% | 2.2 mm | Strongly recommend |
| 1 mm overjet | 16.7% | 33.3% | 1.1 mm | Do not recommend |
| 0 mm overjet | 2.8% | 0% | 0.8 mm | Do not recommend |

FIG. 21

| Actual Size | Bumper Size | Range |
|---|---|---|
| 57.0 mm | 1 L | 54.7 - 57.2 |
| 61.5 mm | 2 L | 57.3 - 63.8 |
| 66.0 mm | 3 L | 63.9 - 68.3 |
| 70.5 mm | 4 L | 68.4 - 72.8 |
| 75.0 mm | 5 L | 72.9 - 77.3 |
| 79.5 mm | 6 L | 77.4 - 81.8 |
| 84.0 mm | 7 L | 81.9 - 86.3 |
| 88.5 mm | 8 L | 86.4 - 91.8 |

FIG. 22

| Years of Age | Maximal Opening (mm) | -2.5 S.D. Opening (mm) | Sample Size | Reference |
|---|---|---|---|---|
| 3-5 | 42 | 34 | 149 | Bernal & Tsamtsoris (1986) |
| 7 | 47 | 39 | 440 | Nilner & Lassing (1981) |
| 8 | 48 | 39 | 440 | Nilner & Lassing (1981) |
| 9 | 49 | 39* | 440 | Nilner & Lassing (1981) |
| 10 | 52 | 40* | 440 | Nilner & Lassing (1981) |
| 11 | 52 | 41* | 440 | Nilner & Lassing (1981) |
| 12 | 53 | 42* | 440 | Nilner & Lassing (1981) |
| 13 | 54 | 43* | 440 | Nilner & Lassing (1981) |
| 14 | 54 | 43* | 440 | Nilner & Lassing (1981) |
| 17 | 56 | 44* | 285 | Wanman & Agerberg (1986) |
| 18 | 57 | 45* | 275 | Wanman & Agerberg (1986) |
| 19 | 58 | 45* | 264 | Wanman & Agerberg (1986) |

FIG. 23

SYSTEM AND METHOD FOR DETERMINING AN ORTHODONTIC DIAGNOSTIC ANALYSIS OF A PATIENT

CROSS-REFERENCE TO RELATED APPLICATIONS

This application is a continuation of U.S. patent application Ser. No. 14/294,404 filed Jun. 3, 2014, the complete disclosure of which is hereby expressly incorporated in its entirety herein by this reference.

BACKGROUND OF THE INVENTION

The present invention relates to an orthodontic assessment of a patient. More specifically, the present invention relates to a system and a method for determining an orthodontic diagnostic analysis of a patient at various dental maturity stages with predictions of future conditions and/or treatment recommendations.

It is generally known to provide dental care to a patient. Typically, the patient may seek care from a professional at an office visit. The professional may be, for example, a dentist, an orthodontist or other type of oral health care provider. The professional may examine the patient using various techniques. Such techniques may be imaging and/or x-raying the oral area and/or the jaws. After reaching a diagnosis, the professional may then provide the patient with an oral appliance to correct the condition of the patient. In addition to the oral appliance, the professional may provide the patient with instructions for exercises to perform while wearing the oral appliance. The exercises may cause, for example, the teeth to move toward a corrected position and may assist in correcting a malocclusion.

Diagnostic decisions may often be made by a single look at the patient by the professional. The professional may estimate what may be present in the dentition of the patient. The examination may not entail a deeper and/or more detailed study. However, the thoroughness of the examination may seriously impact the future of the patient. For example, the individual deciding the best alternative for a patient may have little understanding of how future development of the various problems may influence the outcome of the future health of a patient. Several analytical procedures that may be significant may seldom be used to make a diagnosis for a patient. The patient may ultimately suffer as a result. A typical example may be an arch-length analysis. The arch-length measurement may accurately predict if sufficient room may be available to straighten crowded teeth and/or rotated teeth. However, the arch-length analysis may be time consuming for the professional. As a result, some arch-length analyses may provide an inaccurate assessment.

Another important consideration in the assessment of the dental health of the patient may be the age of the patient. For example, dental maturity may be generally categorized into five age groups of which four groups may be segregated according to dental maturity stages. The four stages may be the full deciduous dentition from about two years of age or three years of age up to about five and one-half years of age or six years of age. The permanent lower incisors may begin to erupt at about five and one-half years of age to six and one-half years of age. The period during which the adult incisors may begin and finish their full eruption may be at about seven years of age or eight years of age may be called the transitional period. The next dental maturity stage may be called the mixed-dentition period when the other permanent teeth, such as, for example, canines, first premolars, second premolars and the permanent second molars may erupt into place. This period may last from about eight years of age to twelve years of age. The next dental maturity stage may be the adult dentition where twenty-eight permanent teeth may be fully erupted and where jaw growth may still be active up to about eighteen years of age in a female and about twenty years of age in a male. The final dental maturity stage may be during the adult dentition after most of the jaw growth may be complete. Although both males and females grow slightly after this period, this minimal growth is not generally important for orthodontic treatment.

Most orthodontics may be done during the late mixed stage and the early adult dentition from about eleven years of age to thirteen years of age. Some orthodontics may be done during the mixed dentition after the permanent upper and lower permanent incisors may be erupted. Orthodontics are infrequently used before or during the eruption of the adult incisors. Performing orthodontics during the transitional eruption period may have the advantage that the teeth may be aligned before the collagenous fibers may be formed. The orthodontics may minimize relapse tendencies and may lessen the length of treatment to about twenty percent of the average time consumed for fixed orthodontics for patients of eleven years of age to thirteen years of age.

Treatment with fixed and/or removable appliances during the transitional period on patients of six years of age to eight years of age and earlier on patients of two years of age to six years of age may be beneficial in malocclusion treatment. The early period with patients of two years of age to six years of age may be recommended for sleep-disordered breathing problems. The treatment may either advance the mandible and tongue or may prevent the lower jaw from displacing posteriorly while sleeping. The treatment may teach the patient to breathe through the nose instead of the mouth which may correct the snoring and may improve the behavioral symptoms caused by breathing problems.

Child patients that may have a prominent mandible may be helped at a young age by treatment to slow adverse changes that may occur during the growing years. Further types of correction that may improve breathing may entail improving abnormal swallowing, correcting anterior open bites, correcting a narrowed maxilla and improving speech problems. Such early problems may have significant effects on the future health and well-being of the patient.

In general dentistry, oral surgery, maxillofacial surgery and/or orthodontics, malocclusions may be assessed clinically or radiographically using cephalometrics. One such common condition of a malocclusion may be overbite, in which the top teeth and/or the lower teeth of the patient do not align properly. Cephalometric analysis may be the most accurate way of determining types of malocclusions, since such analysis may include assessments of skeletal body, occlusal plane angulation, facial height, soft tissue assessment and anterior dental angulation. Various calculations and assessments of the information in a cephalometric radiograph may allow the clinician to objectively determine dental relationships and/or skeletal relationships and determine a plan of correction.

If a non-surgical alternative may produce results comparable with those that may be achieved surgically, then the professional may consider and/or may suggest such a non-surgical approach to the patient. In some cases, a non-surgical approach may be the preferred choice of the professional and/or the patient.

For example, facial growth modification may be an effective method of resolving skeletal Class III jaw discrepancies in growing children. Dentofacial orthopedic appliances may be used. Orthognathic surgery in conjunction with orthodontic care may be required for the correction of malocclusions in an adult patient.

A need, therefore, exists for a system and a method for determining an orthodontic diagnostic analysis of a patient at various dental maturity stages with predictions of future conditions and/or treatment recommendations. A need also exists for a system and a method that may use a computer for determining an orthodontic diagnostic analysis of a patient at various dental maturity stages with predictions of future conditions and/or treatment recommendations. A need also exists for a system and a method for determining an orthodontic diagnostic analysis of a patient at various dental maturity stages with predictions of future conditions and/or treatment recommendations that may use an oral appliance.

SUMMARY OF THE INVENTION

The present invention relates to an orthodontic assessment of a patient. More specifically, the present invention relates to a system and a method for determining an orthodontic diagnostic analysis of a patient at various dental maturity stages with predictions of future conditions and/or treatment recommendations.

To this end, in an embodiment of the present invention, a system is provided. The system has an imaging component configured to locate landmarks in a mouth of a patient. The imaging component locates the landmarks and generates imaging data of the landmarks. A central processing unit has access to a database with information associated with orthodontic conditions. The central processing unit receives the imaging data from the imaging component and generates measurements associated with landmarks and dentition in the mouth of the patient. The central processing unit predicts orthodontic conditions of the patient based upon the measurements and the information in the database and recommends treatments to the patient based upon the predicted orthodontic conditions.

In another embodiment of the present invention, a method is provided. Diagnostic programs associated with characteristics of developing dentition of a patient are provided. An initial assessment of the patient corresponding to the developing dentition of the patient is performed. The initial assessment uses an imaging device to locate points in a mouth of the patient and generates imaging data. The imaging data is transferred to a central processing unit which obtains measurements associated with selected points in the mouth of the patient and predicts future orthodontic conditions of the patient based upon the measurements. A report of findings of the initial assessment is provided to the patient with treatment recommendations based upon the findings.

In yet another embodiment of the present invention, a further method is provided. Points in a mouth of a patient are located with an imaging device. The imaging device locates the points and generates imaging data of the points in the mouth. The imaging data is transferred to a central processing unit which has access to a database having information associated with orthodontic conditions. The central processing unit generates measurements associated with selected points and dentition in the mouth of the patient using the imaging data. The central processing unit predicts orthodontic conditions of the patient based upon the measurements and the information in the database. Treatments are recommended to the patient based upon the predicted orthodontic conditions which are based on the imaging data and the information in the database.

It is, therefore, an advantage of the present invention to provide a system and a method for determining an orthodontic diagnostic analysis of a patient.

Another advantage of the present invention is to provide a system and a method for determining an orthodontic diagnostic analysis of a patient which may provide a diagnostic analysis of orthodontic and associated problems for a patient from two years of age through adulthood.

Yet another advantage of the present invention is to provide a system and a method for determining an orthodontic diagnostic analysis of the patient which may provide measurements of the dentition of the patient that may be repeated to determine the progress achieved during treatment.

Another advantage of the present invention is to provide a system and a method for determining an orthodontic diagnostic analysis of a patient which may provide a level of unbiased accuracy of measurements on which insurance providers may rely.

An advantage of the present invention is to provide a system and a method for determining an orthodontic diagnostic analysis of a patient which may provide the incidence of each symptom to educate a patient and/or a parent of the patient as to the relative frequency of the particular symptom.

Still another advantage of the present invention is to provide a system and a method for determining an orthodontic diagnostic analysis of a patient which may provide information about a future risk that a symptom may remain abnormal at a future time in the life of the patient, such as, for example, at twelve years of age or eighteen years of age.

A further advantage of the present invention is to provide a system and a method for determining an orthodontic diagnostic analysis of a patient which may provide a prediction of an amount of the measured symptom that may be expected in the future.

Moreover, an advantage of the present invention is to provide a system and a method for determining an orthodontic diagnostic analysis of a patient which may provide treatment recommendations whether the certain problems should be corrected at a certain time.

Further, an advantage of the present invention is to provide a system and a method for determining an orthodontic diagnostic analysis of a patient which may allow a parent to make an informed conclusion on whether treatment for his or her child may be appropriate.

A further advantage of the present invention is to provide a system and a method for determining an orthodontic diagnostic analysis of a patient which may provide an estimate of the future stability of the corrected problem and/or an expected relapse of the result.

Another advantage of the present invention is to provide a system and a method for determining an orthodontic diagnostic analysis of a patient which may require the professional to answer each question required by the system and the method using a computer program and as a result may require the professional to check several symptoms that may not have previously been considered.

Moreover, an advantage of the present invention is to provide a system and a method for determining an orthodontic diagnostic analysis of a patient wherein the system and the method may use a computer to identify points required for a diagnosis.

Another advantage of the present invention is to provide a system and a method for determining an orthodontic diagnostic analysis of a patient which may provide the patient with a diagnosis similar to a second opinion.

A further advantage of the present invention is to provide a system and a method for determining an orthodontic diagnostic analysis of a patient wherein parameters of treatment may be altered to suit various orthodontic philosophies.

Another advantage of the present invention is to provide a system and a method for determining an orthodontic diagnostic analysis of a patient wherein various appliance philosophies may be altered to suit the preference of the professional responsible for the treatment.

Yet another advantage of the present invention is to provide a system and a method for determining an orthodontic diagnostic analysis of a patient which may use a computer program to accomplish a diagnosis in a short time period and/or in an efficient manner.

Still further, an advantage of the present invention is to provide a system and a method for determining an orthodontic diagnostic analysis of a patient which may use a computer program to consider various diagnoses for specific ages and dental development.

Still another advantage of the present invention is to provide a system and a method for determining an orthodontic diagnostic analysis of a patient which may use a computer program to predict future conditions and/or diagnoses for specific ages and/or dental development.

Also, an advantage of the present invention is to provide a system and a method for determining an orthodontic diagnostic analysis of a patient which may use a computer program to consider various arch measurements and/or dental measurements that change with growth and/or development and/or accommodate these changes into the diagnosis.

Another advantage of the present invention is to provide a system and a method for determining an orthodontic diagnostic analysis of a patient which may use a computer program to determine the circumferential arch where the permanent upper incisors have an excessive overjet and before any upper permanent incisors erupt.

A further advantage of the present invention is to provide a system and a method for determining an orthodontic diagnostic analysis of a patient which may use a computer program to predict the sizes of the permanent teeth prior to their appearance into the mouth by utilizing statistical correlations and/or multiplication factors.

Another advantage of the present invention is to provide a system and a method for determining an orthodontic diagnostic analysis of a patient which may use a computer to predict tooth sizes and/or actual size calculations of the erupted tooth widths to inform the professional of the correct size of a performed appliance.

Yet another advantage of the present invention is to provide a system and a method for determining an orthodontic diagnostic analysis of a patient which may use a computer to determine whether gum tissue may have receded from a tooth and/or the amount of recession and may replicate the measurement to determine damage during treatment.

Still further, an advantage of the present invention is to provide a system and a method for determining an orthodontic diagnostic analysis of a patient which may use a computer to determine if the gingival tissue is swollen and/or inflamed by a color analysis of the gingival tissue.

An advantage of the present invention is to provide a system and a method for determining an orthodontic diagnostic analysis of a patient which may use a computer to determine if any root resorption may be present and/or may be occurring during treatment.

Yet another advantage of the present invention is to provide a system and a method for determining an orthodontic diagnostic analysis of a patient which may use a computer to estimate the severity of a gummy smile and may predict if the gummy smile may be corrected.

An advantage of the present invention is to provide a system and a method for determining an orthodontic diagnostic analysis of a patient which may use a computer to determine the future of a profile of the patient.

Also, an advantage of the present invention is to provide a system and a method for determining an orthodontic diagnostic analysis of a patient which may use a computer program to provide pictures of similar malocclusions to the patient to indicate what a malocclusion may look like in the future if no treatment may be initiated.

Still another advantage of the present invention is to provide a system and a method for determining an orthodontic diagnostic analysis of a patient which may be more complete than what may typically be done by personal observation of the patient.

A further advantage of the present invention is to provide a system and a method for determining an orthodontic diagnostic analysis of a patient which may provide objective measurements and/or data to the patient.

Yet another advantage of the present invention is to provide a system and a method for determining an orthodontic diagnostic analysis of a patient of based upon an age range of the patient.

An advantage of the present invention is to provide a system and a method for determining an orthodontic diagnostic analysis of a patient of a person while permanent teeth and/or deciduous teeth may be present and/or erupting in the mouth.

A further advantage of the present invention is to provide a system and a method for determining an orthodontic diagnostic analysis of a patient by guiding the erupting teeth into a desired position in the mouth.

Yet another advantage of the present invention is to provide a system and a method for determining an orthodontic diagnostic analysis of a patient which may be repeated at time intervals, for example, every three months, to verify if a patient may be experiencing progress to continue to obtain a desired result at the end of treatment.

Still further, an advantage of the present invention is to provide a system and a method for determining an orthodontic diagnostic analysis of a patient which may eliminate and/or reduce additional x-ray radiation exposure of the patient.

An advantage of the present invention is to provide a system and a method for determining an orthodontic diagnostic analysis of a patient which may eliminate potential discomfort of taking impressions for study models.

Further, an advantage of the present invention is to provide a system and a method for determining an orthodontic diagnostic analysis of a patient which may eliminate wasteful and/or unnecessary records and/or examinations for specific developmental stages of the dentition.

Moreover, an advantage of the present invention is to provide a system and a method for determining an orthodontic diagnostic analysis of a patient which may provide appliances of various sizes to correct malocclusions and straighten the teeth at various ages in the deciduous, mixed and/or adult dentitions and either prevent problems from developing and/or correcting the same problems.

Still further, an advantage of the present invention is to provide a system and a method for determining an orthodontic diagnostic analysis of a patient which may control the eruption of teeth and/or depress certain teeth to correct the malocclusion.

Yet another advantage of the present invention is to provide a system and a method for determining an orthodontic diagnostic analysis of a patient which may straighten the teeth to avoid braces and/or other types of orthodontics.

In accordance with another aspect of the present invention, a method is provided comprising the steps of: providing a plurality of diagnostic programs associated with characteristics of developing dentition of a patient; performing an initial assessment of the patient corresponding to the developing dentition of the patient wherein the initial assessment uses an imaging device to locate points in a mouth of the patient wherein the imaging device generates imaging data; transferring the imaging data to a central processing unit wherein the central processing unit obtains measurements associated with selected points in the mouth of the patient and predicts future orthodontic conditions of the patient based upon the measurements; and providing a report of findings of the initial assessment to the patient with treatment recommendations based upon the findings.

In accordance with still another aspect of the present invention, a system is provided comprising: an imaging component configured to locate landmarks in a mouth of a patient wherein the imaging component locates the landmarks and generates imaging data of the landmarks; and a central processing unit having access to a database with information associated with orthodontic conditions wherein the central processing unit receives the imaging data from the imaging component and generates measurements associated with landmarks and dentition in the mouth of the patient and further wherein the central processing unit predicts orthodontic conditions of the patient based upon the measurements and the information in the database and recommends treatments to the patient based upon the predicted orthodontic conditions.

In accordance with yet another aspect of the present invention, a method is provided comprising the steps of: locating points in a mouth of a patient with an imaging device wherein the imaging device locates the points and generates imaging data of the points in the mouth; transferring the imaging data to a central processing unit wherein the central processing unit has access to a database having information associated with orthodontic conditions; obtaining measurements associated with selected points and dentition in the mouth of the patient wherein the central processing unit generates the measurements using the imaging data; measuring a width of the arch from an upper canine cusp to an opposite upper canine cusp and from a lower canine cusp to an opposite lower canine cusp and multiplying the width by separate factors to indicate a proper distance along a curve that the dentition may occupy; measuring a point from the middle of a mesiobuccal cusp on a first side of the mouth to a point on a center of a first molar on a second side of the mouth around an arch of the dentition to determine a recommended size of a bumper for an appliance; predicting orthodontic conditions of the patient based upon the measurements and the information in the database wherein the central processing unit provides predictions based on the imaging data and the information in the database; and recommending treatments to the patient based upon the predicted orthodontic conditions wherein the central processing unit provides recommendations based on the imaging data and the information in the database.

Additional features and advantages of the present invention are described in, and will be apparent from, the detailed description of the presently preferred embodiments and from the drawings.

BRIEF DESCRIPTION OF THE DRAWINGS

FIG. 5 illustrates a chart for use in an embodiment of a method in accordance with the present invention.

FIG. 6 illustrates a chart for use in an embodiment of a method in accordance with the present invention.

FIG. 7 illustrates a chart for use in an embodiment of a method in accordance with the present invention.

FIG. 8 illustrates a chart for use in an embodiment of a method in accordance with the present invention.

FIG. 9 illustrates a chart for use in an embodiment of a method in accordance with the present invention.

FIG. 11 illustrates a chart for use in an embodiment of a method in accordance with the present invention.

FIG. 12 illustrates a chart for use in an embodiment of a method in accordance with the present invention.

FIG. 13 illustrates a chart for use in an embodiment of a method in accordance with the present invention.

FIG. 14 illustrates a chart for use in an embodiment of a method in accordance with the present invention.

FIG. 15 illustrates a chart for use in an embodiment of a method in accordance with the present invention.

FIG. 16 illustrates a chart for use in an embodiment of a method in accordance with the present invention.

FIG. 17 illustrates a chart for use in an embodiment of a method in accordance with the present invention.

FIG. 18 illustrates a chart for use in an embodiment of a method in accordance with the present invention.

FIG. 19 illustrates a chart for use in an embodiment of a method in accordance with the present invention.

FIG. 20 illustrates a chart for use in an embodiment of a method in accordance with the present invention.

FIG. 21 illustrates a chart for use in an embodiment of a method in accordance with the present invention.

FIG. 22 illustrates a chart for use in an embodiment of a method in accordance with the present invention.

FIG. 23 illustrates a chart for use in an embodiment of a method in accordance with the present invention.

DETAILED DESCRIPTION OF THE PRESENTLY PREFERRED EMBODIMENTS

The present invention relates to an orthodontic assessment of a patient. More specifically, the present invention relates to a system and a method for determining an orthodontic diagnostic analysis of a patient at various dental maturity stages with predictions of future conditions and/or treatment recommendations.

Figure 1:
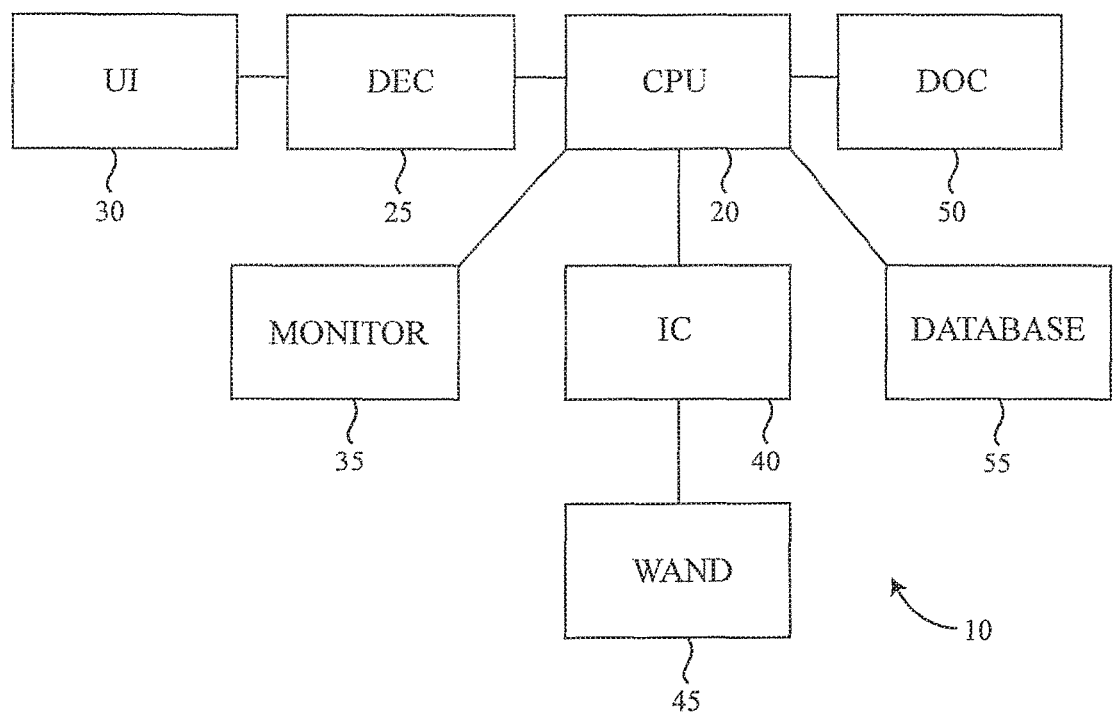
FIG. 1 illustrates a block diagram of an embodiment of a system in accordance with the present invention.

Referring to the drawings wherein like numerals represent like parts, FIG. 1 illustrates a system 10 in an embodiment of the present invention. The system 10 may be used for diagnosing the orthodontic needs and requirements of the patient. The system 10 may be useful in assisting orthodontic practitioners. Also, the system 10 may permit a diagnosis of the dentition and/or conditions of the patient. The system 10 may provide instructions to the user.

In an embodiment, the system 10 may use a computer to perform certain parts of the assessment. For example, U.S. Pat. No. 6,582,225 entitled "Dental diagnosis and dispensing apparatus and a system and a method for providing same" issued on Jun. 24, 2003 and U.S. Pat. No. 5,882,192 entitled "Computerized orthodontic diagnosis and appliance dispenser" issued on Mar. 16, 1999 disclose using a computer in a dental diagnosis. Applicant of the present application is common to each reference and hereby incorporates by reference each of these patents in their entirety in this disclosure.

The system 10 may have multiple components. For example, the system 10 may have a central processing unit 20 (hereinafter referred to as a "CPU"). The CPU 20 may be a microprocessor, a computer and/or the like. The CPU 20 may evaluate data transmitted to the CPU 20 by the components of the system 10. Further, the CPU 20 may control the components of the system 10. The CPU 20 may be programmed by one skilled in the art to evaluate data and to control the components of the system 10.

In addition, the system 10 may have a data entry component 25 (hereinafter referred to as a "DEC"). The DEC 25 may have a user interface 30 (hereinafter referred to as a "UI"). The UI 30 may allow the user to enter information to be processed by the CPU 20 prior to, during, and/or after examination by the system 10. Such information may be data related to the patient, such as, for example, age, race, gender and/or the like. The UI 30 may be a keyboard, for example, or any other means for entering characters, data and/or information to be processed by the CPU 20. The UI 30 may have a plurality of lettered and/or numbered input keys for manual data entry and/or may be a touch screen or other suitable device. Further, the UI 30 may have a microphone to allow the user to enter data and/or commands by voice. One having ordinary skill in the art may recognize various other alternatives for the UI 30 within the scope of the present invention. The present disclosure is not intended to be limited to the examples given.

The system 10 may also have a monitor 35 which may allow the user to see the information entered by the user into the DEC 25. The monitor 30 may provide high-resolution images to the user. The monitor 35 may be a plasma display, an LED display or an LCD display. The monitor 35 may relay information from the system 10 to the user.

In addition, the monitor 35 may display instructions for the user relating to proper use of the system 10. For example, the instructions may give an outline for an examination so that the user may be required to complete one step of the examination before proceeding to the next step of the examination. The outline may ensure that the examinations are complete and/or performed in a standardized manner. Successive examinations may be repeated at a later date and may be compared to the earlier examinations. As a result, data from the earlier examinations may be compared in a direct relationship to data collected in a later examination conducted in the same manner.

The system 10 may also have an imaging component 40 (hereinafter referred to as "IC"). The IC 40 may take images of a portion of an interior of a mouth and/or an exterior of a face of the patient. The IC 40 may take images, whether, digital, still, video, digital X-ray or the like, by means of a camera or any other image capturing device known by those skilled in the art. The images from the IC 40 may be transferred to the CPU 20 for evaluation.

The system 10 may also have a wand 45 which may be used in conjunction with the IC 40. The wand 45 may have multiple capabilities. For example, the wand 45 may be capable of taking high resolution images of the interior of the mouth of the patient. The dentition of the patient may be visually captured by the wand 45. The oral cavity may be fully imaged by the wand 45. The wand 45 may take images of the dentition and may transmit the images to the CPU 20.

During the initial examination, the dentition of the patient may be digitized by the wand 45 that may be passed around the mouth of the patient. The wand 45 may pass over the buccal, labial, occlusal and lingual surfaces of the teeth as well as the gum lines. The wand 45 may also pass over the patient with the teeth occluded. Images of the dentition of the patient may be registered on the monitor 35. Any aspect of the dentition may be viewed from any angle. The wand 45 may be used to take a profile view of the face and/or a frontal view of the face of the patient. The wand 45 may be used to take a wide open view for a joint analysis and/or a high smile view. The imaging of the dentition using the wand 45 may be non-invasive and may take about two minutes to five minutes. The wand 45 may provide a one-to-one image of the dentition of the patient.

The wand 45 may also take images of the biting surfaces of the patient. Further, the wand 45 may take images of the exterior of the mouth of the patient. The wand 45 may transmit the images to the CPU 20. The CPU 20 may process the images of the dentition to create a virtual model of the interior of the mouth of the patient. The virtual model may be displayed on the monitor 35. The CPU 20 may process the images of the biting surfaces and the exterior of the mouth of the patient to create further virtual models of the patient. The CPU 20 may combine the images of the dentition and the images of the biting surfaces with the exterior of the mouth of the patient to enhance the virtual models and/or to provide more detail.

In addition, the system 10 may locate landmarks within the mouth of the patient. For example, the system 10 may use the wand 45 in cooperation with the CPU 20 may locate the landmarks within the mouth of the patient. The wand 45 may transmit measurements of certain landmarks to the CPU 20.

In an embodiment, the system 10 may locate approximately fifty individual landmarks, most of which may be on the dentition of the patient and a portion of the landmarks may be on the face of the patient. The landmarks may encompass the widths of the upper anterior teeth and the widths of the lower anterior teeth. The teeth may be deciduous or permanent. The landmarks may indicate anterior available space and/or posterior available space for the teeth in the upper arch and/or the lower arch. The landmarks may indicate a vertical overbite and/or an open bite, a horizontal overjet and/or a mandibular protrusion, freeway space and a maximum jaw opening.

Further, the landmarks may indicate estimates of tooth widths of unerupted teeth and/or erupted permanent teeth. The estimates may be calculated using various multiplication factors and a mesio-distal width of a lower permanent central incisor. The lower permanent central incisor may be highly correlated with the sizes of the other permanent teeth in the mouth whether erupted or unerupted. As a result, a required space for sizes of various permanent teeth that may be either erupting into the mouth yet erupted may be determined. Thus, an assessment of future crowding may also be determined.

The system 10 may also determine the curvature of the lower arch and the upper arch from the canine-to-canine arch width using a multiplication factor. The CPU 20 may measure along a line of the curvature of the arch along with apparent broken contacts and/or hidden broken contacts under tissue to obtain a reading of the arch curvature. The arch curvature may be used to estimate position and dimensions regardless of the severity and malposition, particularly of the upper incisors in an excessively incisal protrusion case. The estimates of broken contacts and/or rotations may allow the CPU 20 to predict crowding.

From the various landmarks, freeway space and a maximum mandibular opening may be obtained. Gingival recession, if present, may also be obtained. Color of the gingival tissue may be observed. The color may be normal or red in color which may indicate a periodontal problem for the patient.

By using the landmarks, the crowding and/or the spacing, as well as the arch length analysis data of the incisal or anterior portion of the upper and lower arches and the posterior upper and lower segments of the arch, the degree of crowding may be determined. Also, the landmarks may indicate whether sufficient space may be available for correction of the crowding or if additional appliances, such as bumpers, head gears, expansion appliance and/or full fixed orthodontics may be required to achieve a successful result. The CPU 20 may also indicate the expected success of retention and/or the amount of relapse that may occur in the future. The CPU 20 may access information in a database 55 to base the predictions on statistical data of treatment results with various appliances used for the correction.

Further, the CPU 20 may use the landmarks by processing the measurements of the landmarks and/or the dentition to make calculations to predict future sizing of the dentition and/or oral conditions of the interior of the mouth of the patient. For example, the CPU 20 may use the measurements and/or the landmarks to estimate the degree of enlargement or reduction required for a diagnosis in terms of calculating the proper size of a tooth and/or the teeth of the patient.

In addition, the CPU 20 may perform the arch-length analysis in such a manner that the procedure may be replicated accurately. Doing so may be helpful in the successful treatment of the patient. Repeating this procedure after a few months of treatment may accurately determine if the patient may be making sufficient progress from the treatment.

Further, the user may input information into the UI 30 of the DEC 25. The UI 30 may transmit the data to the CPU 20. The system 10 may transmit data and/or instructions to the monitor 35 to communicate with the user of the system 10. After the necessary information may have been provided by the user, the CPU 20 may transmit information to the wand 45 and/or the IC 40 to take various digital images of the mouth and the teeth of the patient. If necessary, the CPU 20 may regularly ask questions and/or may instruct the user how to acquire the proper video images. The communication may be performed using the monitor 35 and/or the UI 30 of the DEC 25.

The images, measurements and/or landmarks from the IC 40 may be taken by the wand 45 and may be processed by the CPU 20. Information otherwise gathered by the system 10 may be processed by the CPU 20. The CPU 20 may have a data output component 50 (hereinafter referred to as "DOC"). The information, images, measurements and/or landmarks may be transmitted, electronically or otherwise, by the DOC 50. The DOC 50 may transmit images and/or data to another location, for example, via the internet, electronic mail or other means, for evaluation by another system or individual, such as a doctor, dentist, orthodontist or the like. The DOC 50 may be implemented by one skilled in the art such that the DOC 50 may transmit images and/or data by, for example, the internet, telephony, satellite or other means. Further, the DOC 50 may generate a document for the patient.

In an embodiment, the IC 40 and/or the wand 45 may transmit digital and/or analog signals that may represent the images of the mouth and/or the dentition of the patient to the CPU 20. The CPU 20 may perform calculations and/or a diagnosis based upon the images, preprogrammed information and/or any other information that may be entered by the user. After the diagnosis may be complete, the CPU 20 may instruct the patient about treatments for the specific orthodontic conditions.

In an embodiment, the database 55 may be connected to the CPU 20 of the system 10. The database 55 may store information regarding medical, orthodontic and/or dental conditions, growth charts, multiplication factors for estimations, standardized measurements and/or the like. For example, sizes of dentition for patients of various age ranges may be stored in the database 55.

The database 55 may store information associated with the severity of a medical, orthodontic and/or dental condition. For example, the severity may be identified in one of three categories: minimal, moderate or severe. The database 55 connected to the CPU 20 of the system 10 may store information, such as medical, orthodontic and/or dental standards regarding the degree of an overbite, for example. The CPU 20 may determine if the overbite may be minimal, moderate, or severe based upon images taken by the wand 45 and/or from the IC 40. To this end, ranges may be established for the three categories. Information regarding the patient and the images from the IC 40 may be analyzed by software installed in the CPU 10 to determine in which category the patient may be classified.

For example, an overbite that may be more than a minimal amount may be treatable by a corrective dental appliance. Therefore, if the CPU 20 may determine that the overbite of the patient may be greater than a minimal amount, a corrective dental appliance may be recommended to the patient. However, if the CPU 20 may determine that the degree of overbite is a maximum amount and/or may further determine that the age of the patient may be greater than fifteen years of age, the CPU 20 of the system 10 may deny the patient a diagnosis and/or a dental appliance.

Further, the CPU 20 may access the database 55 for information associated with various sizes of appliances indicated for various problems for patients of different ages. For example, a Nite-Guide® appliance (a registered trademark of Ortho-Tain. Inc.) may be provided in eleven sizes for patients of five years of age to seven years of age or younger. An Occlus-o-Guide® appliance (a registered trademark of Ortho-Tain, Inc.) may be provided in thirteen sizes for patients of eight years of age to twelve years of age. Also, an Ortho-T® appliance (a registered trademark of Ortho-Tain, Inc.) may be provided in thirteen sizes for patients twelve years of age and older. Moreover, various preformed positioners of different types and/or sizes may be stored in the database 55. The appliances and/or positioners may be stored in the database as digitized images. The digitized images of the appliances may be transparent. The system 10 may fit the digitized images of the appliance over a digital model of the dentition of a patient. The professional may see through the transparent digitized image of the appliance to verify if the selected size and/or type of appliance may fit for the specific patient.

Thus, the system may virtually place a preformed appliance over the dentition of the patient to see if the appliance may fit without ever trying the actual appliance in the mouth of the patient. Using the system 10 to test fit the appliance over the digitized dentition of the patient may eliminate the need to sterilize the actual appliance prior to actually trying the appliance in the mouth of the patient. Any size of the digitized image of the appliance may be tried for the proper fit. Thus, keeping a full inventory of the sizes of the appliances may not be required.

Figure 2:
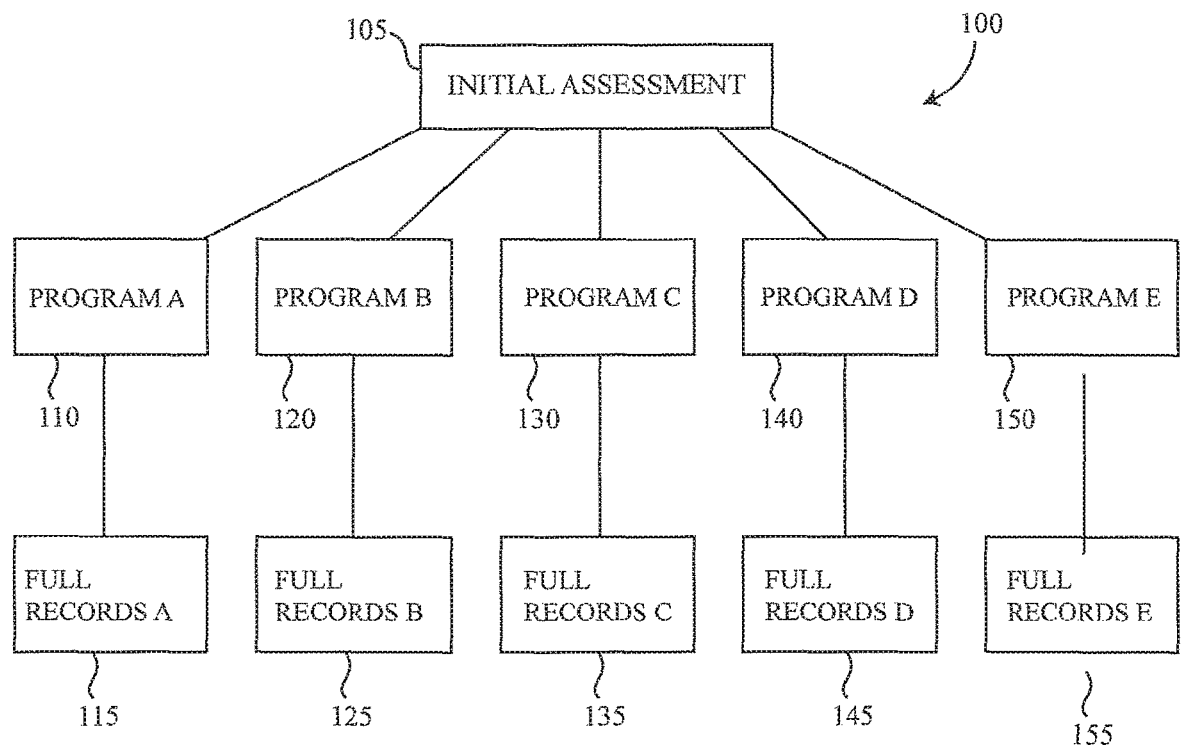
FIG. 2 illustrates a flowchart of an embodiment of a method in accordance with the present invention.

FIG. 2 illustrates a flowchart of a method 100 in an embodiment of the present invention. Embodiments of the present invention disclose the method 100 for assessing, diagnosing and/or reporting orthodontic conditions of a patient. The orthodontic conditions of the patient may depend on the age of the patient, since the dentition of the patient may change and/or may mature within certain age ranges. Therefore, the system 10 and/or the method 100 may be tailored to the age of the patient. To this end, the method 100 may have an initial assessment. The method 100 may have a step 105 in which the initial assessment may be performed on the patient. The initial assessment may be tailored to the age of the patient.

As shown in FIG. 2, step 110 illustrates Program A which may be designed for children and/or patients ranging in age from two and one-half years of age or three years of age to five years of age or six years of age. Program A may be configured to relate to the dentition and/or the oral development of patients in this age range. In particular, patients in this age range may experience the eruption of early deciduous dentition. Thus, Program A may correlate the initial assessment and/or any further examinations of the patient to the specific age of the patient. The correlated initial assessment may focus the initial assessment on the current state of development of the patient. Certain assessments may not be indicated for the age range in Program A. However, other assessments may be critical at the current state of development of the patient. To this end, Program A may be performed as set forth hereinafter.

Further, step 120 illustrates Program B which may be designed for children and/or patients ranging in age from five years of age to seven years of age. Program B may be configured to relate to the dentition and/or oral development of patients in this age range. In particular, patients in this age range may have transitional dentition. Thus, Program B may correlate the initial assessment and/or any further examinations of the patient to the specific age of the patient. The correlated initial assessment may focus the initial assessment on the current state of development of the patient. Certain assessments may not be indicated for the age range in Program B. However, other assessments may be critical at the current state of development of the patient. To this end, Program B may be performed as set forth hereinafter.

Moreover, step 130 illustrates Program C which may be designed for children and/or patients ranging in age from eight years of age to twelve years of age. Program C may be configured to relate to the dentition and/or oral development of patients in this age range. In particular, patients in this age range may have mixed dentition. Thus, Program C may correlate the initial assessment and/or any further examinations of the patient to the specific age of the patient. The correlated initial assessment may focus the initial assessment on the current state of development of the patient. Certain assessments may not be indicated for the age range in Program C. However, other assessments may be critical at the current state of development of the patient. To this end, Program C may be performed as set forth hereinafter.

Step 140 of FIG. 2 illustrates Program D which may be designed for children and/or patients ranging in age from twelve years of age to eighteen years of age. Program D may be configured to relate to the dentition and/or oral development of patients in this range. In particular, patients in this age range may have early permanent dentition. Thus, Program D may correlate the initial assessment and/or any further examinations of the patient to the specific age of the patient. The correlated initial assessment may focus the initial assessment on the current state of development of the patient. Certain assessments may not be indicated for the age range in Program D. However, other assessments may be critical at the current state of development of the patient. To this end, Program D may be performed as set forth hereinafter.

Step 150 of FIG. 2 illustrates Program E which may be designed for children and/or patients ranging in age from eighteen years of age to adulthood. Program E may be configured to relate to the dentition and/or oral development of patients in this range. In particular, patients in this age range may have mature and/or late permanent dentition. Thus, Program E may correlate the initial assessment and/or any further examinations of the patient to the specific age of the patient. The correlated initial assessment may focus the initial assessment on the current state of development of the patient. Certain assessments may not be indicated for the age range in Program E. However, other assessments may be critical at the current state of development of the patient. To this end, Program E may be performed as set forth hereinafter. Therefore, the system 10 and/or the method 100 may be described herein with respect to the defined patient age ranges.

As shown in FIG. 2, step 110 illustrates Program A of the method 100. The system 10 and/or the method 100 may be tailored to children and/or patients that may range from two and one-half years of age or three years of age to five years of age or six years of age. Patients within this age range may experience the eruption of early deciduous dentition. The system 10 and/or the method 100 may have the initial assessment and/or a full records assessment. As shown in FIG. 2, the method 100 may have step 115. Step 115 may be the full records assessment for the patient that may be within the age range for Program A.

In an embodiment, a professional, such as a dental, orthodontic or medical professional, assistant or hygienist for example, (hereinafter, referred to as, "the professional") may perform the initial assessment on the patient. After the initial assessment, the system 10 and/or the method 100 may generate a preliminary and/or initial diagnosis based upon certain determining characteristics of the patient. The system 10 and/or the method 100 may provide such a diagnosis prior to the full records assessment.

For example, in an embodiment, Program A may have seven initial determining characteristics that may be assessed by the professional. The characteristics may be as follows:

1. Any sleep problems (snoring, attention deficit, daytime sleepiness, morning headaches, etc.)
2. Any significant speech problems
3. Mandibular retrusions
4. Temporomandibular Joint ("TMJ") problems
5. Habits, such as mouth breathing, finger sucking, swallowing problems
6. Swollen tonsils or adenoids 7. End-to-end jaw relation and/or a prognathic relation, for example a forward positioning of the mandible Thus, the system 10 and/or the method 100 may generate the preliminary and/or initial diagnosis based the seven determining factors listed without the additional examinations and/or diagnostics of the full records assessment. The system 10 and/or the method 100 may make a decision on the seven determining factors. As a result, the system 10 and/or the method 100 may provide the assessment and/or the diagnosis for treatment recommendations prior to the full records assessment.

Also, the professional may assess several other factors and/or problems of the patient. For example, the professional may assess whether the patient may have any sleeping problems. In particular, the assessment may determine the following:

1. Does the patient have hyperactivity, attention deficit disorder ("ADD"), and/or look sleepy?
2. Does the patient have an excessive overjet and/or a class II relation over three mm?
3. Does the patient mouth breathe, have a narrow palate and/or have habits like thumb-sucking?
4. Does the patient have swollen tonsils?

In the event of a positive response to any of the four questions, the professional may provide a sleep disordered breathing questionnaire to the parent of the patient to obtain further details of the sleep habits of the patient. A positive response to multiple items on the sleep disordered breathing questionnaire may indicate that a recommendation for further records and/or possible treatment may be required.

Also, the CPU 20 of the system 10 may access information in the database 55 that may contain data associated with sleep-disordered breathing. For example, the information may have data arranged by the following categories: symptom, acceptable normal amount, incidence, risk of problem by twelve years of age, resultant problems by twelve years of age and/or treatment recommendations.

In an embodiment, Program A may be used to diagnose and/or treat sleep problems in children. For example, FIG. 11 outlines the most common behavioral symptoms together with snoring and mouth breathing. The information from the database 55 as shown in FIG. 11 may have data related to symptoms with associated acceptable amounts and incidence of occurrence. Further, the information may have data that may relate the symptoms to the likelihood of associated risks and/or resultant problems of the particular symptom. Finally, the information may have treatment recommendations for the symptoms. The data from the database 55 may be used to prepare the preliminary and/or initial assessment and/or diagnosis.

The professional may also determine if the patient may have any speech problems. For example, the professional may inquire whether the patient may be hard to understand, may drop consonants and/or may have a lisp. If so, a speech questionnaire may be provided to the parent of the patient to obtain further details of the speech habits of the patient. The professional may also determine if the patient may have any other problems, such as, an open bite and/or tongue thrust issues. The system 10 and/or the method 100 may recommend further analysis in the event of a positive response to any of the above assessment items.

The system 10 and/or the method 100 may generate a document with findings and/or explanations of the importance and/or the requirements of further analysis for the patient. The document may be generated in an electronic format and/or a hard copy format. The document may be given to the parent of the patient. The professional may provide additional information to the parent of the patient, if required and/or if desired. However, the document may provide the parent of the patient with the preliminary and/or initial assessment and/or diagnosis for the patient.

The document may summarize the problems discovered and/or present with the patient. An assessment and/or description of the seven elements of the initial determining characteristics may be provided in the document. The document may list any of the problems the patient may have and any associated recommendations for treatment. The document may also predict if future treatment may be warranted for the problems that the patient may have. The document may explain the problems related to sleep disorders that cause certain symptoms. For example, the lack of oxygen in the blood because of the restriction of the airway may result in high blood pressure and other serious heart problems.

In an embodiment, the system 10 and/or the method 100 may measure several other conditions. For example, mandibular retrusions may be measured by identifying a landmark on the upper central incisal edge and measuring the distance parallel to the posterior occlusal plane to the contact with the lower central incisor. Mandibular retrusions, the size of the adenoids and/or the antero-posterior width of the nasopharynx and the oropharynx may be determined during the full records assessment that may use a cephalometric x-ray film and/or a 3-D film.

In an embodiment, the system 10 and/or the method 100 may measure overjet of the patient and may predict the expected overjet by twelve years of age. The system 10 and/or the method 100 may provide treatment recommendations. The system 10 and/or the method 100 may obtain the recommendations for particular severities of overjet that may be determined by comparison with standards.

For example, treatment for any overjet of three mm or more may be recommended in the deciduous dentition if the patient has sleep problems. Treatment for any overjet over four mm may be recommended to prevent potential sleep problems from developing in the patient. FIG. 12 illustrates the overjet that may be corrected, particularly if sleep problems are suspected in the patient. Overjet may cause problems for the patient when associated with sleep problems. However, overjet may be corrected at this age.

In an embodiment, the document may contain data related to the particular measurements of the overjet and specific treatment recommendations. For example, the document may state that an overjet of four mm has a strong risk of being associated with airway constriction and may be corrected at this age.

TMJ problems may be a problem in young children, and treatment may be important if present. The professional may examine the patient for TMJ problems, for example, by performing a physical examination and/or asking a series of questions associated with TMJ. The symptoms of TMJ may be checked at the initial examination and may be verified during the full records assessment.

The professional may also inquire about certain habits that the patient may have. For example, such habits may be swallowing problems, mouth breathing, thumb sucking and/or finger sucking and/or the like. Also, speech habits and/or problems may be determined. The speech questionnaire may be provided to the parent of the patient to obtain further details of the speech habits of the patient.

The professional may investigate whether the patient may snore and, if so, the frequency of the snoring. For example, if the patient may snore frequently and/or habitually, the professional may examine the patient to determine whether the adenoids and/or the tonsils may be swollen. If the adenoids and/or the tonsils have major swelling or if the patient may have difficult nasal breathing, the patient may be referred to a pediatrician or an ear, nose and throat ("ENT") specialist.

The professional may also investigate whether the patient may breath easily through the nose, may have difficulty with nasal breathing or may not be able to breathe through the nose. Other observations may be whether the patient may have a retrognathic mandible and/or excessive overjet. A further observation may be whether the patient snores only when on his or her back or snores in any position.

The sleep disordered breathing questionnaire may indicate that the patient may have labored, difficult and/or loud breathing at night, may have interrupted snoring where breathing stops for two seconds to four seconds, and/or may have stoppage of breathing more than twice in one hour. In these situations, the professional may refer the patient to a pediatrician and/or a sleep specialist.

The professional may initially diagnose end-to-end jaw relations and a prognathic mandible and may recommended correction to help control any progression. Further confirmation may be made with a lateral cephalometric x-ray film or 3-D film in the full records assessment. Various measurements may be made to confirm and to estimate the severity of the problem.

In an embodiment, the initial assessment and diagnosis may be sufficiently complete to recommend further records, imaging and/or treatment recommendations. The document may be provided to the parent of the patient. The document may outline the initial treatment recommendations and may contain data of the findings. The document may describe the treatment time and fee. The document may also have pictures of other similar cases of patients at twelve years of age, for example, as a result of non-treatment.

In an embodiment, the system 10 and/or the method 100 may also encompass the full records assessment of Program A as shown in step 115 of FIG. 2. As part of the full records assessment, the professional may take x-rays of the patient. For example, the x-rays may contain a digital panoramic x-ray film of the patient, a lateral digital cephalometric x-ray film, and/or one 3-D x-ray film. The 3-D x-ray film may be preferred since details may be clearer to see in such an x-ray. The imaging in the full records assessment may contain intra-oral and/or facial photographs.

The professional may perform an oral examination of the patient as part of the full records assessment. The professional may review the completed sleep disordered breathing questionnaire and/or the speech questionnaire. If the sleep disordered breathing questionnaire may indicate that the patient may have labored, difficult, loud breathing at night, may have interrupted snoring where breathing stops for two seconds to four seconds and/or may have stoppage of breathing more than twice in one hour, the professional may refer the patient to a pediatrician and/or a sleep specialist. Further, the patient may require a home night study to check for possible apnea or hypopnea. The home night study may indicate that the patient may have sleep apnea in which breathing may cease for four seconds or more and may occur more than twice per hour. The home night study may indicate that the patient may have hypopnea in which the patient may have labored breathing. Such positive indications may require a referral to a sleep specialist. Positive responses to seven or more items on the sleep disordered breathing questionnaire may indicate that the patient may have sleep-disordered breathing that may warrant correction. The treatment may depend upon other symptoms the patient may have such as mouth breathing, habitual or periodic snoring, narrow palate, retrognathic mandible and/or the like.

The professional may verify whether the patient may be able to breathe through his or her nose during the full records assessment. If not, the professional may check if the palate may be narrow. The palate may be compared to a normal amount. If the palate may be an abnormal amount, the palate may require widening. If the palate may be of a normal width, the professional may refer the patient to a pediatrician to check for deviated septum and/or swollen adenoids and/or tonsils.

The full records assessment may require a further TMJ examination to observe clicking, a deviated opening, a maximum opening, pain, a difficult opening and/or difficult chewing as may have been observed at the initial examination. If any of these problems may exist, except limited opening, the patient may be treated. If the patient may have the limited opening, the professional may refer the patient to a TMJ specialist. Information about the TMJ may have been given after the initial examination.

The professional may consider habits of the patient as part of the full records assessment. For example, if the child sucks his or her thumb and/or fingers during the day, the problem may be a serious one. Typically, the patient may reduce the sucking habit after starting school. If the thumb sucking and/or finger sucking may be causing an open bite under in a patient five years of age, the open bite may be corrected, particularly if the patient mouth breathes during the day. Other habits that may cause the palate to be narrow, such as swallowing problems, tongue-thrusting and/or sucking habits, may be corrected to prevent the habit from affecting the palate width.

The professional may review any speech problems from the speech questionnaire that indicate that a sleep problem may exist. The professional may question the parent of the patient in detail about the sleep problems, particularly snoring, hyperactivity, attention deficit, daytime sleepiness and mouth breathing. Such problems may be the five most important symptoms.

Figure 3:
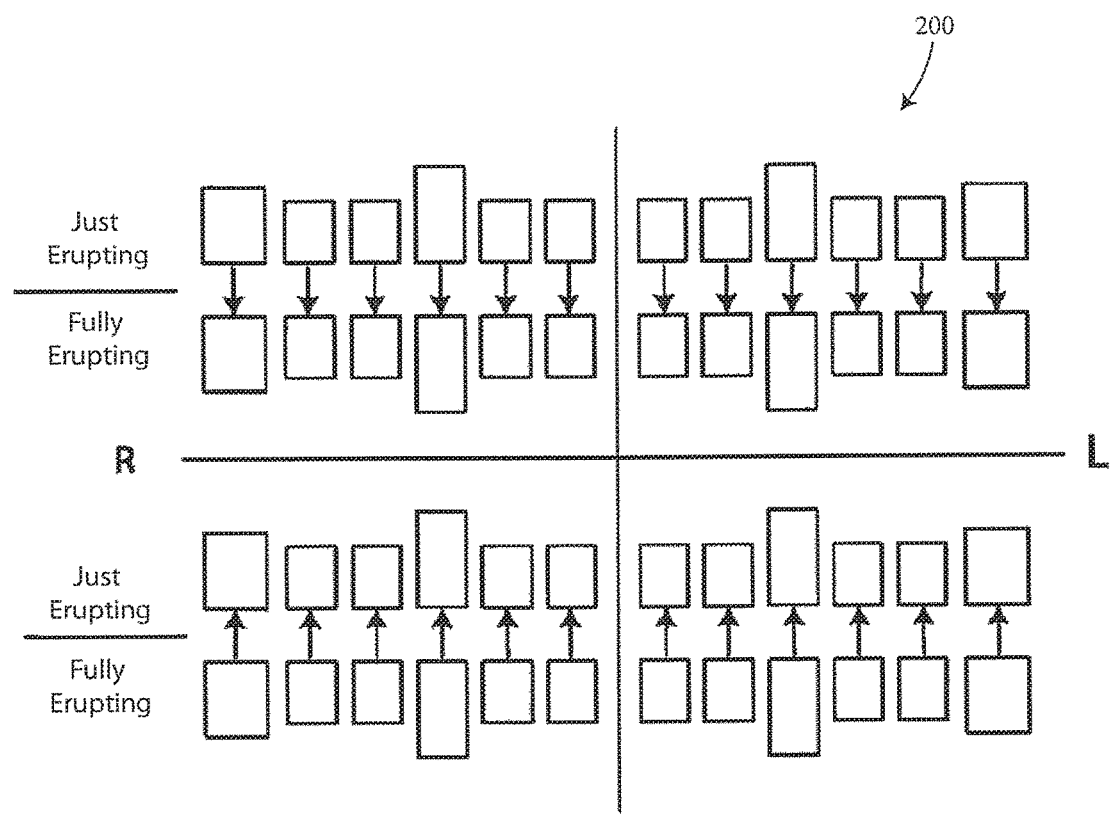
FIG. 3 illustrates a schematic diagram of a dentition chart in an embodiment of the present invention.

The professional may analyze the panoramic film and/or the 3-D film, if available, as part of the full records assessment. The panoramic film and/or the 3-D film may be analyzed by the system 10 and/or the method 100. For example, the CPU 20 may analyze the panoramic film and/or the 3-D film to ensure that all unerupted teeth may be present. The professional may also perform this review. If any permanent teeth may be missing, the missing teeth may be charted. For example, FIG. 3 illustrates a dentition chart 200. The dentition chart 200 may have placeholders, such as boxes, for example to represent the dentition of the mouth. The relative placement of the dentition may be organized on the dentition chart 200. The erupted teeth may be indicated on the dentition chart 200.

The professional may physically examine the unerupted teeth by the using the system 10 to ensure the unerupted teeth may be in the proper respective positions to erupt into the arch. The professional may chart the dentition on the dentition chart 200. Any teeth not erupting in the proper respective positions may also be charted on the dentition chart 200. The professional may determine whether any extra teeth exist and/or whether the extra teeth may require removal now and/or in the future. The professional may also examine the patient for any other observable problems present such as cysts, tumors, abscesses, bone problems and/or the like.

The professional may also analyze the cephalometric x-ray and/or the 3-D film during the full records assessment. The professional may use the system 10 and/or the method 100 to take three measurements of the nasopharynx. Certain anatomical parts may be located and measured. For example, a measurement of a narrowed distance from the uvula to the post wall of pharynx may be made. The thickness of the uvula may be measured. A measurement from the tip of the uvula to the post wall of the pharynx may be made. A measurement of the oropharynx from the base of the tongue to the posterior wall of the pharynx may also be made.

Measurements may be taken to determine whether the amounts may be normal or abnormal. If any nasopharynx measurements may be abnormal, the professional may check for potential causes, such as, for example, whether the adenoids and/or the tonsils may be swollen. Any swollen tonsils and/or adenoids may be referred to the pediatrician for possible removal if the patient may be considered to have a breathing problem.

If any nasopharynx measurements may be abnormal, the professional may check for potential causes, such as whether the upper arch may be narrow. The system 10 may measure dimensions in area across the canines, the deciduous first molar, the deciduous second molar and/or the first permanent molars. The CPU 20 may determine from information from the database 55 whether the measurements may be normal or abnormal and may also provide treatment recommendations.

The professional may further analyze the cephalometric x-ray and/or the 3-D film during the full records assessment. The professional may use the system 10 to take measurements of the retrognathic position of the maxilla and the mandible. The professional may locate several landmarks using the system 10, such as, for example, points Ba, A, B, N, Gn, Po, Me, the tip of the upper and the lower incisors, Co, ANS, PNS, Go.

The system 10 may measure the following linear distances: Ba-A, Ba-B, ANB, overjet, Co-Gn, N-Me, Ba-PNS and ANS-Me. The CPU 20 may compare the linear distances to normal and abnormal measurements. To this end, the CPU 20 may access information from the database 55. If the overjet, ANB, Bo-A and Ba-B may be abnormal, the professional may make a recommendation for treatment if the patient may be suspected of having sleep problems.

If any nasopharynx measurements may be abnormal, the professional may check for potential causes, such as, for example, an open bite. The system 20 may measure any evidence of an open bite. If the open bite may be accompanied by a sucking habit, treatment may be strongly recommended. Further, the system 10 may measure an end-to-end jaw relation and any Class III tendency. If either may exist, treatment may be strongly recommended, particularly if a skeletal Class III may be less than three mm. Finally, the CPU 20 may identify a tip of the two lower deciduous canines and may multiply this distance by a factor of 0.926 to obtain the arch curvature of the incisal available space. The system 10 and/or the method 100 may also measure the curvature along the incisal edges of the lower four deciduous incisors to also obtain the available space. The upper dentition may be assessed in the same manner. The CPU 20 may access the database 55 to determine a size of an appliance that may be recommended for use.

The full records assessment shown in step 115 of FIG. 2 may utilize the system 10 to determine and/or to list any findings that may result from the full records assessment and/or other analysis. The full records assessment may have any recommended treatments and/or procedures indicated by the analysis of the oral examination, the panoramic and/or 3-D film and/or the cephalometric and/or 3-D film. Thus, the system 10 and/or the method 100 may provide the initial assessment and the full records assessment and/or analysis of the early deciduous dentition of the patient of three years of age to five years of age.

As a result of the initial assessment and/or the full records assessment, an appliance may be recommended treatment for the patient as part of an overall treatment plan. For example, the system 10 may have information in the database 55 related to the appliance and/or whether the appliance may be indicated for a particular condition. FIG. 5 illustrates a collection of information that may be accessed related to recommendations for appliances from the CPU 20. In an embodiment, the CPU 20 may access the information in FIG. 5 from the database 55. FIG. 5 may list symptoms of the patient, the appliance most applicable to the symptoms of the patient and/or the recommended uses of the appliance. Various habit correctors and youth appliances may be listed. In particular, certain appliances may be listed by name. For example, the Nite-Guide® appliance may be worn at night for certain problems. Thus, the CPU 20 of the system 10 may access the database 55 to determine an appropriate appliance for the patient.

As shown in FIG. 2, step 120 illustrates Program B of the method 100. Program B may be designed for children and/or patients ranging in age from five years of age to seven years of age. Program B may be configured to relate to the dentition and/or oral development of patients in this range. In particular, patients in this age range may have transitional dentition. Thus, Program B may correlate the initial assessment and/or any other examinations of the patient to the specific age of the patient. The correlated initial assessment may focus the initial assessment on the current state of development of the patient. Certain assessments may not be indicated for the age range in Program B. However, other assessments may be critical at the current state of development of the patient. To this end, Program B may be performed as set forth hereinafter.

In an embodiment, any one of the following problems may be require a treatment recommendation and/or the full records assessment shown in step 125 of FIG. 2. The problems may be as follows:

1. Crowding/spacing in which a lower arch and an upper arch length analysis may be performed to determine whether the patient may be a candidate for treatment. Other problems, such as, for example, displaced teeth with space shortage, missing teeth and various other problems may be examined and noted by the professional.

2. Overbite greater than one and one-quarter mm and/or an open bite of any severity 3. Overjet greater than three mm and/or a Class III relation of any severity including zero mm which may be an end-to-end or pseudo Class III relation 4. Cross-bites of any severity 5. TMJ having any two symptoms except for limited opening 6. Habits such as, for example, thumb sucking, finger sucking, swallowing, speech problems and/or mouth breathing 7. Suspected sleep-disordered breathing problems 8. Narrow upper arch The system 10 and/or the method 100 may generate the document for the patient. The document may summarize whether any of the above eight items may be problems that may be considered beyond normal. The document may also explain why the full records assessment and/or probable treatment may be recommended. The document may contain the treatment time required, the patient responsibility, any fee involved, probabilities of success and any possible relapse. The document may have pictures that may illustrate what the teeth may look like without performing any treatment.

The CPU 20 may generate and/or print the document for the parent of the patient with findings for the parent to consider and/or study. For example, the document may be configured as shown in FIG. 6. The document may be generated after the initial assessment 105 may be performed in step 120 of Program B of the method 100 and prior to step 125 in which the full records assessment may be conducted.

Further, the professional, the dental assistant or the hygienist may examine the patient and indicate on the monitor 35 his/her answers. For example, the examination may determine whether the teeth present may be only deciduous except for the first permanent molars. If so, the examination may determine whether the lower deciduous incisors may be straight with no crowding and no spacing. The examination may determine whether any permanent teeth may be present. If so, the professional may examine the patient and indicate the permanent teeth on the dentition chart 200 on the monitor 35.

The professional may also determine whether the upper incisors and/or the lower incisors, either deciduous or permanent, may be crooked. If not, the professional may examine the patient and indicate whether any deciduous teeth may be absent and may indicate the absent teeth on the dentition chart 200. Further, if any teeth may be absent, the professional may examine the patient and/or may indicate whether the space may be partially or completely closed. The professional may determine whether any permanent teeth may be erupting though tissue and/or may have fully erupted.

The professional may also perform a decay check if required by a school, for example. The dentition chart 200 may be filled out with a separate document indicating the number of suspected cavities present for the patient on a separate sheet. The teeth that may be suspected of having decay may be indicated on the dentition chart 200. As a result, the patient may require a visit to a dentist for treatment.

The professional may examine the patient further and indicate on the monitor 35 his/her answers. For example, the professional may determine whether the patient may have an open bite. If so, the professional may determine whether the open bite may be due to a habit and/or may be skeletal. Further, the professional may determine whether the patient may have a Class III problem, an end-to-end, pseudo Class III problem and/or a skeletal Class III problem. Also, the professional may determine whether the patient may have any anterior and/or posterior cross-bites or a narrow palate.

The professional may examine the patient further and input his/her answers with the UI 30. For example, the examination may determine whether the patient may have TMJ. The examination may involve checking for the following TMJ issues:
  a) sporadic or frequent clicking
  b) frequent or infrequent pain and/or headaches
  c) opening deviation or difficulty in opening
  d) difficult chewing
  e) limited opening with only two fingers The professional may also examine the patient further and may enter his/her answers with the UI 30. The examination may determine whether the patient may have certain habits, for example. The examination may check for the following habits:
  a) swallowing problems and/or tongue thrusting
  b) mouth breathing during the night only or during the day and the night
  c) speech problems, for example, a lisp or difficulty to understand the speech of the patient
  d) thumb sucking and/or finger sucking during the night only or during the day and the night The professional may scan the dentition, the profile of the face with teeth occluded and the front of the face with teeth occluded. The professional may observe a frontal high smile and a frontal wide open mouth that may show upper and lower incisal edges.

The system 10 may identify various landmarks after the professional may scan the dentition. The CPU 20 may identify landmarks from a scanned study cast of dentition or the professional may personally identify the landmarks by hand. Using the wand 45 of the IC 40 to scan the mouth of the patient may provide a digitized dentition that may be more reliable, consistent and unbiased. The following landmarks may be identified:
  a) an upper incisal edge and/or a lower incisal edge of one central incisor that may be on the left or the right whichever may be clearer and straight, the central incisor may be deciduous or permanent if fully erupted
  b) mesial of the upper deciduous canines and/or the lower deciduous canines
  c) mesial and distal of the upper centrals and/or the lower centrals and laterals which may be deciduous or permanent if erupted
  d) tip of the cusp of the upper canines and the lower canines
  e) distal of the deciduous canines and distal of the second deciduous molars if there may be a shortage of posterior space due to loss of teeth and/or decay
  f) the center point on the occlusal surface of all deciduous upper molars and/or lower molars The CPU 20 may perform an arch length analysis of the lower incisal area and/or the upper incisal area. For example, when only deciduous lower incisors may be present, the lower arch length analysis may be performed. The landmark identified in the landmark d) above, namely the tip of the deciduous canine to the tip of other canine may be multiplied by a factor of 0.926, and four may be added to the result. The final number may be the available space of lower incisor area. Also, the system 10 and/or the CPU 20 may measure the curve of the arch between mesial of the canines.

If only deciduous incisors may be present, the mesial-distal widths of the lower four deciduous incisors may be subtracted from the available space calculated above to obtain any spaces present. The spaces between the teeth and/or crowding of the deciduous incisors may determine whether treatment may be recommended. The CPU may access information in the database 55 and compare the measurements to the information in the database 55 to determine whether treatment may be recommended. The information may further indicate the incidence, the future risk of malocclusion and/or the prediction of crowding by a certain age for each measurement. Such information may be provided to the parent of the patient.

Also, if a permanent lower incisor may be showing, the CPU 20 may multiply the mesial-distal width of the lower central incisor by four and add one to obtain the required space. The available space less the required space may equal an arch shortage, an arch excess or may be normal. If any arch shortage greater than one mm may be present, treatment may be strongly recommended regardless of what the upper may be. The CPU 20 may access information in the database 55 and compare the measurements to the information in the database 55 to determine whether treatment may be recommended. When the lower arch length analysis may be done and the first permanent lower incisor or any number of lower incisors may have broken though the tissue, the CPU 20 may access information in the database 55 to obtain how much room may be expected to develop depending on which teeth have erupted.

For example, the information in the database may describe which teeth may have fully erupted at the time of the initial exam. The information may also state how much expansion may occur up to about eight years of age. Therefore, the lower available space calculation described above may be calculated using the tip of the deciduous lower canine to the tip of the opposite canine on other side multiplied by the factor of 0.926 with four added to the result. The result may represent the expansion expected from the eruption of the lower incisors. However, the four mm may have to be altered in that the added four may change since each permanent tooth that has fully erupted has reduced the amount. Therefore, the CPU 20 may access other information in the database 55.

For example, if both of the lower permanent centrals may be fully erupted, the other information may indicate that only one mm of future arch expansion may be left. Thus, the available space formula may be calculated using the tip of the deciduous lower canine to the tip of the opposite canine on other side multiplied by the factor of 0.926 with one added to the result to obtain the lower available space. Once the available space may be determined, the required space may be measured from the mesial-distal width of one lower permanent central multiplied by four with one mm added for the two laterals. The required space may be subtracted from available space. The result may represent crowding with a negative number, excess with a positive number or may be normal if the result may be zero. The CPU 20 may access information in the database 55 and may compare the measurements to the information in the database 55 to determine whether treatment may be recommended.

The CPU 20 may access information in the database 55 to obtain the parameters of treatment when greater lower crowding than seven mm may be present and may indicate when a limited amount of further treatment may be needed. Such further treatment may use a bumper or a headgear which may produce an extra three mm. Such further treatment may require an additional fee, and the CPU 20 may be present the fee amount in the document to the patient. Also, the information in the database 55 may provide extreme limits that may not be treated even with a bumper and may recommend when a patient may require a specialist for fixed orthodontics.

Further, the information in the database 55 may provide the total lower space that may be available from forceful expansion and from stripping the deciduous lower molars to yield the total space that may be available for the correction of the crowding. If the Nite-Guide® appliance procedure may be started at the correct time as the first lower permanent central breaks tissue, seven mm of correction may be available with the appliance alone. If more crowding than this may be present, the use of the bumper may provide an extra three mm, so the total possible space created with Nite-Guide® appliance and the bumper may be ten mm. Values over eleven mm may be referred out to a specialist for fixed orthodontics.

In an embodiment, to calculate the proper size of the bumper, a measurement may be made by the CPU 20. The CPU 20 may measure a distance from a point two mm buccally opposite the center of the mesio-buccal cusp of the lower first molar or the upper first molar to estimate the size of an upper bumper. The measurement may be made from either the left side or the right side. A measurement may be made from this point to the same point on the opposite side, two mm buccal from the center of the mesial-buccal cusp, exactly around the arch keeping the line of measure two mm away from the buccal and labial surfaces of the teeth at the gingival margin. The measurement may be made at the most prominent and/or the widest position of the teeth bucco lingually and slightly occlusally from the gingival margin. If the upper incisors may be severely tipped labially, the measurement may be made at the gingival margin two mm labial to this gingival margin and not at the incisal edges of these upper incisors. This measurement may be used for the proper size of the bumper according to FIG. 17.

In an embodiment, the CPU 20 may compare the obtained measurement with information in the database 55. For example, FIG. 22 illustrates information related to the sizes of the bumpers. The measurement may be within a certain range which may indicate the bumper size number. The actual size of the bumper may also be provided in FIG. 22.

In an embodiment, data related to TMJ problems and TMD diagnosis may be used by the system 10. Certain symptoms may be incorporated into the CPU 20. For example, TMJ sounds may be recorded by the system 10. The frequency, amplitude and type may be sampled by a device similar to a stethoscope that may be placed over each TMJ. As the patient opens and closes, the device may record the sounds of clicking and crepitus. The TMJ sounds may be recorded in normal occlusion as well as an advanced position which may eliminate the clicking sounds. The recording may be repeated after a treatment period to verify progress and/or improvement.

Also, the sound of the patient snapping teeth together may be recorded. A solid one-sound noise or a multi-sound noise when occluding the teeth together may determine if the occlusion may be well coordinated or may have various interferences. Areas of improper contact on occlusion may be located.

A video may be made of the opening and closing movements of the patient. The video may be digitally recorded. A single straight line may be present on opening and closing movements. Various lateral excursions may be recorded. An image of the maximum opening of the jaw may be measured in mm and may be compared to normal and abnormal opening mouths according to various ages as listed in FIG. 23.

Moreover, the CPU 20 may access information in the database 55 and may compare the measurements to the information in the database to determine if a case may be corrected when various lower permanent incisors may be present. Any crowded dentition from six and one-half mm up to ten mm of crowding may be corrected, depending on what teeth have already erupted and whether the Nite-Guide® appliance may be used alone with stripping of the posterior deciduous molars or if an additional bumper may be required.

Moreover, the information in the database 55 may provide the total lower space that may be available after various permanent incisors have already fully erupted. The total lower space may be the expansion possible due to the eruption of the permanent incisors plus the stripping of the post deciduous molars. To obtain the projected crowding and/or spacing and the recommendations for treatment to be presented to the parent, the required space may be subtracted from the available space to obtain the degree of crowding or spacing present. The information in the database 55 may be used to inform the parent about the lower arch condition of the patient.

Although the lower arch may be primarily used for the diagnosis, the CPU 20 may perform an arch length analysis of the upper incisal arch. The upper arch length analysis may be performed in a similar manner to the analysis of the lower arch length. When only the deciduous upper incisors may be present, the upper arch length analysis may be performed. The tip of the upper deciduous canine to the tip of opposite deciduous canine on the other side may be multiplied by a factor of 0.9932, and seven may be added to the result. The final number may be the available space of the upper.

The mesial-distal width of the lower permanent central, if erupted, may be measured to get the approximate sizes of the upper permanent teeth. For example, the size of the upper permanent central may be equal to the size of the lower permanent central incisor multiplied by a factor of 1.61. The size of the upper permanent lateral may be equal to the size of the lower permanent central incisor multiplied by a factor of 1.23. The total required upper may be determined by adding together the upper permanent central incisor and the upper permanent lateral incisor and multiplying by two. The CPU 20 may access information in the database 55 and may compare the measurements to the information in the database 55 to determine the amount for future enlargement expected when various permanent teeth may already be erupted. In the same manner as in the lower arch calculation, various upper permanent incisors may be present with gradual reductions in the remaining space created by the full eruption of the upper permanent incisors. The required space in the upper arch may be obtained in the same way as above.

A shortage of more than one mm of the upper permanent incisors may be strongly recommended for treatment. One mm may be treated for aesthetics, but most parents do not want any crowding to be present in the upper arch. However, the lower may usually be the diagnostic arch to determine whether treatment may be needed. The upper arch findings may be presented to the parent of the patient.

If no permanent upper incisors or permanent lower incisors may be partially showing through tissue and the deciduous incisors upper and lower may be present, the upper arch length analysis may be performed. The upper available space may be determined by measuring the tip of the upper deciduous canine to tip of the deciduous canine on the opposite side and multiplying by a factor of 0.9932 with seven added to the result. The final number may be the available space of the upper deciduous area. The required space may be estimated which may be more difficult since no permanent lower central incisor may be present for measurement initially. However, the treatment may not be started until one lower permanent incisor may be showing.

If all permanent lower incisors may be present, the CPU 20 may perform the arch length analysis by measuring widths of the four lower permanent incisors and also by measuring the curvature of the arch of the lower from the mesial of the canine to the other canine mesial and subtracting the actual tooth size from the curvature of the arch which may equal the available space to get the shortage, the excess or no crowding.

The upper arch length analysis may be done in a similar way except if there may be an overjet with the upper incisors in a forward position. The CPU 20 may position the curvature two mm anterior to the lower incisal arch curvature and may measure the distance from the mesial of one upper canine to the mesial of the other canine to obtain the upper available space. The upper required space may be obtained by either measuring the width of the upper permanent central incisor and multiplying it by 3.5262 or by multiplying the width of the lower permanent central incisor by 5.6776 or by 1.3385 or by multiplying the upper canine to canine width by 1.0363. The width of one upper permanent central may equal the width of the lower permanent central multiplied by the factor of 1.6082. The width of one upper permanent lateral may equal the width of the lower permanent central multiplied by the factor of 1.2287. The upper permanent lateral may also be determined by multiplying the upper central by the factor of 0.7631. Therefore, if an upper lateral may be peg-shaped or with smaller laterals, these calculations of the lateral may give the amount that a normal sized lateral should be with bonding to make an undersized lateral look normal.

The system 10 may also calculate other dental conditions. For example, overbite, defined by a vertical overlap of the front incisors, may be determined. The overbite may be measured from a point on the incisal edge of the upper deciduous or permanent upper central to a point on the edge of the lower deciduous and/or the permanent lower central incisor located parallel to the occlusal plane. This may provide an overbite measure. The CPU 20 may access information in the database 55 to obtain the parameters to estimate future problems for the overbite and/or to recommend treatment.

Open-bite may also be measured. Additional records may be recommended for any incidence of open-bite, with the exception of a skeletal open-bite. Open-bites due to habits may also warrant a strong indication for the full records assessment and/or possible treatment.

Overjet is defined by the horizontal distance from the upper deciduous or permanent central to the lower deciduous or permanent central parallel to the occlusal plane. The CPU 20 may measure the overjet from the incisal edge of the upper central incisor to the lower central incisor incisal edge measured parallel to the occlusal plane. The CPU 20 may access information in the database 55 to obtain the parameters to estimate future problems for the overjet and/or to recommend treatment.

Further, a Class III relation may be measured. The Class III relation may occur when the upper deciduous or permanent central as well as the other upper incisors may be behind the lower deciduous or permanent incisors known as skeletal Class III or in an end-to-end relation. Pseudo Class III may occur when the lower jaw may slip forward after contact in an end-to-end position.

The system 10 may measure from the incisal edge of the lower deciduous or permanent central to the edge of the same deciduous or permanent incisor on the upper parallel to the occlusal plane. Any end-to-end or Class III relation regardless of severity may indicate a strong recommendation for records and/or the possibility for treatment.

Cross-bites may be measured. For example, the professional may indicate whether an anterior or posterior cross-bite may exist. The CPU 20 may also determine the cross-bite. The CPU 20 may access information in the database 55 to indicate to the parent if a cross-bite may be present, the type of cross-bite, front, rear or both and/or the treatment recommendations.

TMJ problems may be indicated. For example, the professional may report any problems with TMJ, and a report to the parent of the patient may be generated. The CPU 20 may access information in the database 55 to indicate to the parent if the TMJ may be present and/or the treatment recommendations.

The professional may also determine habits of the patient and/or to indicate any problem to the parent. For example, thumb sucking habits, which may cause weak teeth, abnormal swallowing, narrow palate and mouth breathing, may be treated. Speech problems may also require treatment. Suspected sleep disordered breathing may be warrant a recommendation to contact a pediatrician and/or a sleep specialist.

In addition, the professional may examine the width of the upper arch to see if the upper arch may appear narrow. The CPU 20 may locate points in the center of the posterior teeth including the upper canine tips, the center of the premolars, the deciduous molars and the permanent molars. The CPU 20 may access information in the database 55 to obtain the parameters to indicate the upper arch width and the abnormal amounts that may warrant expansion in a child patient. If a severe narrowing of the maxilla may be seen particularly with crowded incisors at six years of age to eight years of age, together with nasal breathing problems, a rapid palatal expansion appliance may be recommended. This appliance, with the same symptoms, may be recommended up to about twelve years of age to fourteen years of age, with care taken if the mid-sagittal suture has closed, particularly in females. For males, the appliance may be recommended for patients of about fourteen years of age to sixteen years of age.

The CPU 20 may provide the document as shown in FIG. 6 with the findings for the parent to study. The document may be produced at end of the initial exam. The CPU 20 may summarize what may be considered beyond normal of any of the above eight items and briefly explain why the full records assessment and probable treatment may be recommended, treatment time, the responsibility of the parent and/or the patient, the fee involved, possible success, any possible relapse and pictures what teeth may look like if no treatment may be done.

The CPU 20 may present the findings to the parent of the patient in the document together with a document of the initial diagnostic findings of the system 10. The document may summarize the various problems a child may have, namely crowding, overbite, overjet, cross-bite, TMJ, habits and suspected sleep-disordered breathing problems and a narrow upper arch.

Information regarding cross-bites may be input by the initial examining person or determined by the CPU 20, however, such symptoms as various habits present, or headaches, temporomandibular joint clicking, deviated opening and difficulty in chewing may be input by the examining individual but printed out by the CPU 20 in the same way as crowding, overbite and overjet. As a result, an initial examination may indicate to the patient and/or the parent, within about ten minutes, an unbiased, objective diagnosis with minimal variation and/or an analysis of the eight major components of a malocclusion.

As a result, the patient and/or the parent of the patient may have an extensive report regarding the problems present with the relative severity, percentage of incidence, future predictions of development and what effect treatment may have in the future. The patient and/or the parent may have an understanding of the dental problems and may be able to make an educated decision regarding treatment options presented. The CPU 20 may also provide the fee and the length of treatment for each condition for the patient. The CPU 20 may provide relapse information and/or treatment stability information.

The document from the CPU 20 may summarize these factors as to whether the measure may be normal or abnormal, the incidence of occurrence, and the percentage risk for being a problem at a future time, such as by twelve years of age, by eighteen years of age and/or by some other age. The document may provide what the initially-measured amount may be expected to be in the future, whether any treatment may not be recommended, may be minimally recommended, or may be strongly recommended. The document may provide an indication of whether a future analysis may be recommended and/or whether treatment may be recommended. The document may provide the fee for the treatment, an estimated length of the treatment and the estimated success of the treatment.

If the patient or parent may decide to proceed with the treatment, the patient may have the full records assessment. This analysis may have panoramic x-ray films and cephalometric x-ray films or a 3-D x-ray film taken and analyzed by the CPU 20 program. Other factors such as a problematic gummy smile, sleep problems which involve a questionnaire for the parent to fill out involving several associated factors such as snoring incidence, hyperactivity, attention deficit, restless sleep, poor school performance, daytime sleepiness, mouth breathing, tooth grinding, bed wetting and several other commonly associated problems that may indicate sleep-disordered breathing and sleep apnea, swelling of the tonsils and adenoids and speech problems may be also checked by the professional. The professional may enter the information into the CPU 20 for analysis and to produce an informative review of the various problems. If necessary, the problems may require orthodontic treatment consideration or a referral to a pediatrician or sleep specialist, for example.

Several other factors may be observed and/or reported by the professional, such as, for example, impacted or missing teeth observed on x-ray films, thickness of the mandibular body, any evidence of root resorption, various measures from a cephalometric film such as measure of basion to points A and B and the SNA, SNB, ANB, mandibular plane angle, face height measures, and measures of the nasopharyngeal and oropharyngeal width and volume. If any canines that were measured for a canine-to-canine distance may be displaced from their normal position either labially, lingually or forward or posteriorly that would adversely affect the arch curvature where the teeth may be located. Any unusually shaped teeth such as double incisors or undersized or peg-shaped upper lateral incisors, midline relations. Many of these landmarks may be positions of teeth, presence or absence of various teeth, unusual shapes of teeth and the various landmarks, angles and linear cephalometric measures may be identified and measured by the CPU 20 to eliminate variation caused by human errors in identification.

As shown in FIG. 2, step 120 illustrates Program B of the method 100. The method 100 may have the initial assessment and/or the full records assessment. As shown in FIG. 2, step 125 of the method 100 may be the full records assessment for a patient that may be within the age range for Program B.

In the full records assessment for Program B, the professional may take two x-ray films. For example, a digital panoramic x-ray film of the patient and/or a lateral digital cephalometric x-ray film may be taken. Also, a 3-D film may be taken that may replace the digital panoramic x-ray film of the patient and the lateral digital cephalometric x-ray film.

In the full records assessment for Program B, the professional may perform an oral examination that may check the freeway space of the patient. The professional may either mark a point on the nose of the patient and on the bottom of the chin of the patient. The professional may physically measure the distance at rest and again at occlusion. In an embodiment, the CPU 20 may also indicate the point on the nose and chin and a digitized image may be taken with the wand 45 with the patient at rest and also at occlusion. The CPU 20 may measure the distance and may subtract one from the other to obtain the amount of the freeway space. Any patient with an excessive freeway space, such as seven mm or more, for example, may be checked for a lateral posterior tongue thrust and may require an additional removable appliance.

The CPU 20 may locate a point in the lower level of the upper lip and at the gingival tissue line on the crown of the upper central incisor, either deciduous or permanent. A measurement may be made of the amount of gingival display or gummy smile showing during a high smile. Any patient with a gummy smile of more than two mm may have a gummy smile by twelve years of age. A gummy smile of three mm at six years of age will have a one mm gummy smile at twelve years; however the Nite-Guide® appliance may be able to prevent three mm of a gummy smile. Any deciduous overbite of two mm, for example, if added to the three mm of gummy smile may prevent that amount of gummy smile. Therefore, three mm of improvement added to the deciduous overbite may equal the amount of gummy smile that may be prevented. For example, a three mm improvement plus a two mm deciduous overbite may equal a five mm total of gummy smile that may be prevented.

If a posterior cross-bite may be present, the professional may determine if the posterior cross-bite may be a functional or a dental cross-bite. The professional may enter the information into the system 10 using the UI 30. The CPU 20 may recommend a type of treatment. For example, with a functional cross-bite, bilateral expansion may be recommended. With a dental cross-bite, an Occlus-o-Guide® appliance with placement of a cross-bite wire may be recommended.

The professional may analyze the panoramic x-ray film to determine if any unerupted permanent teeth may be missing. The professional may indicate any missing teeth on the dentition chart 200. If teeth may be missing, the CPU 20 may determine if any premolars may be missing and/or whether treatment may be possible. If severe crowding of greater than four mm may exist, a bumper with the Occlus-o-Guide® appliance may be used. If crowding of greater than eight mm may exist, the professional may refer the patient to a specialist for possible fixed treatment. If several teeth may be missing, the CPU 20 may refer the patient to a specialist for fixed treatment. If any teeth may be erupting in wrong position and/or may have root resorption, or if any cysts, abscesses, extra teeth and/or any other unusual problems may be present, the professional may decide on extraction of extra teeth and/or other treatments.

The professional may analyze the cephalometric/x-ray film. Several landmark points may be located by the CPU 20 and/or may be identified by the professional. The following landmark points may be located by the CPU 20: basion, sella, nasion, points A, B, ANS, Menton, gnathion, condilion, porion, orbitale, PNS, long axis of upper and lower central incisors. Various measurements may be made on the size of airway at two distances from the uvula to the posterior wall of the nasopharynx and from the base of the tongue to the posterior wall of the oropharynx. The CPU 20 may access information in the database 55 to compare these measurements to norms for normal and abnormal amounts. The CPU 20 may indicate if the airway may be normal or abnormal using the information from the database 55 and/or may recommend reasons for treatment. Further, standard cephalometric analyses may be performed by the CPU 20. Also, the professional may perform other analyses, such as Northwestern Reidel, Downs, Steiner, Sassouni, Harvold, Wits, Rickets, McNamara and/or others, as desired.

The overbite and overjet may be measured in the same way as before, and treatment may be recommended. The adenoid tissue may be estimated if significantly swollen. If the adenoid tissue may be swollen, the patient may be referred to a specialist. If upper canine angulation may be excessively abnormal, the professional may recommend a fixed orthodontic appliance treatment procedure.

The professional may determine the number of permanent incisal broken contacts observed prior to their eruption. Typically, three or more indicate a strong recommendation for treatment. For example, one broken contact may equal −1.1 mm crowding; two broken contacts may equal −1.7 mm; three broken contacts may equal −2.8 mm; four broken contacts may equal −4.0 mm; and five broken contacts may equal −5.1 mm of crowding.

If any of the above problems from the final records assessment may indicate that the treatment recommendation due to multiple missing teeth, root resorption, improper angulation of upper canines and/or impacted teeth cannot be rectified with a bumper and an Occlus-o-Guide® appliance, the professional may refuse treatment and may recommend a fixed orthodontic appliance treatment procedure.

In the full records assessment, the professional may determine the skeletal age of the patient and may know the chronological age of the patient. The CPU 20 may calculate the predicted height of the patient using information from the database 55 and may also predict the growth in height expected each year. The percentage increase in height for each following year may also be accessed from the database 55 by the CPU 20. The percentage multiplied by the predicted height may give the height increase for each year to maturity.

Moreover, the profile of the patient may be oriented on the profile template analysis shown in FIGS. 15 and 16 using the appropriate template according to the N-Me distance of the patient. Certain areas of the profile may be abnormal, such as recessive lips, protrusive nose, receding chin, long vertical face, short upper lip and/or long chin. Such areas may fall outside of template margins. The normal profile characteristics, such as the forehead and the upper part of the nose may be kept within the template margins. The CPU 20 may provide a visual tracing of the profile of the patient within the template that may show what ideally may be corrected. The proper treatment, such as advancement of the mandible, retraction of protrusive teeth, lengthening of the face, and/or the like, may be recommended and may be watched to try and achieve proper treatment goals.

A report of any findings from the full records assessment may be reported to the parent of the patient as before. The CPU 20 may generate a document to the parent of the patient describing the abnormal symptoms and treatment recommendations.

As shown in FIG. 2, step 130 illustrates Program C of the method 100. Program C may be designed for children and/or patients ranging in age from five years of age to seven years of age. Program C may be configured to relate to the dentition and/or oral development of patients in this range. In particular, patients in this age range may have mixed dentition. Thus, Program C may correlate the initial assessment and/or examinations of the patient to the specific age of the patient. The correlated initial assessment may focus the initial assessment on the current state of development of the patient. Certain assessments may not be indicated for the age range in Program C. However, other assessments may be critical at the current state of development of the patient. To this end, Program C may be performed as set forth hereinafter.

The system 10 and/or the method 100 may have the initial examination and/or assessment. The full records assessment may also be required. The patient may undergo the initial examination by the professional. The system 10 and/or the method 100 may generate the preliminary and/or initial assessment and/or diagnosis based upon the initial examination of the patient. The system 10 and/or the method 100 may provide such an assessment and/or diagnosis prior to the full records assessment.

In an embodiment, any one of the following problems may be require a treatment recommendation and/or the full records assessment shown in step 135 of FIG. 2. The problems may be as follows:

1. Crowding/spacing in which a lower arch and an upper arch length analysis may be performed to determine whether the patient may be a candidate for treatment. Other problems, such as, for example, displaced teeth with space shortage, missing teeth and various other problems may be examined and noted by the professional.

2. Overbite greater than one and one quarter mm and/or an open bite of any severity 3. Overjet greater than one and one quarter mm) and/or a Class III relation of any severity including zero mm which may be an end-to-end or pseudo Class III relation 4. Cross-bites of any severity 5. TMJ having any two symptoms except for limited opening 6. Habits such as, for example, thumb sucking, swallowing, speech problems and/or mouth breathing 7. Suspected sleep-disordered breathing problems 8. Narrow upper arch The system 10 and/or the method 100 may generate the document for the patient. The document may summarize whether any of the above eight items may be problems that may be considered beyond normal. The document may also explain why the full records assessment and/or probable treatment may be recommended. The document may contain the treatment time required, the patient responsibility, any fee involved, probabilities of success, any possible relapse. The document may have pictures that may illustrate what the teeth may look like without performing any treatment.

The CPU 20 may generate and/or may print the document for the parent of the patient with findings for the parent to consider and/or study. For example, the document may be configured as shown in FIG. 6. The document may be generated after the initial assessment 105 may be performed in step 130 of Program C of the method 100 and prior to step 135 in which the full records assessment may be conducted.

Figure 4:
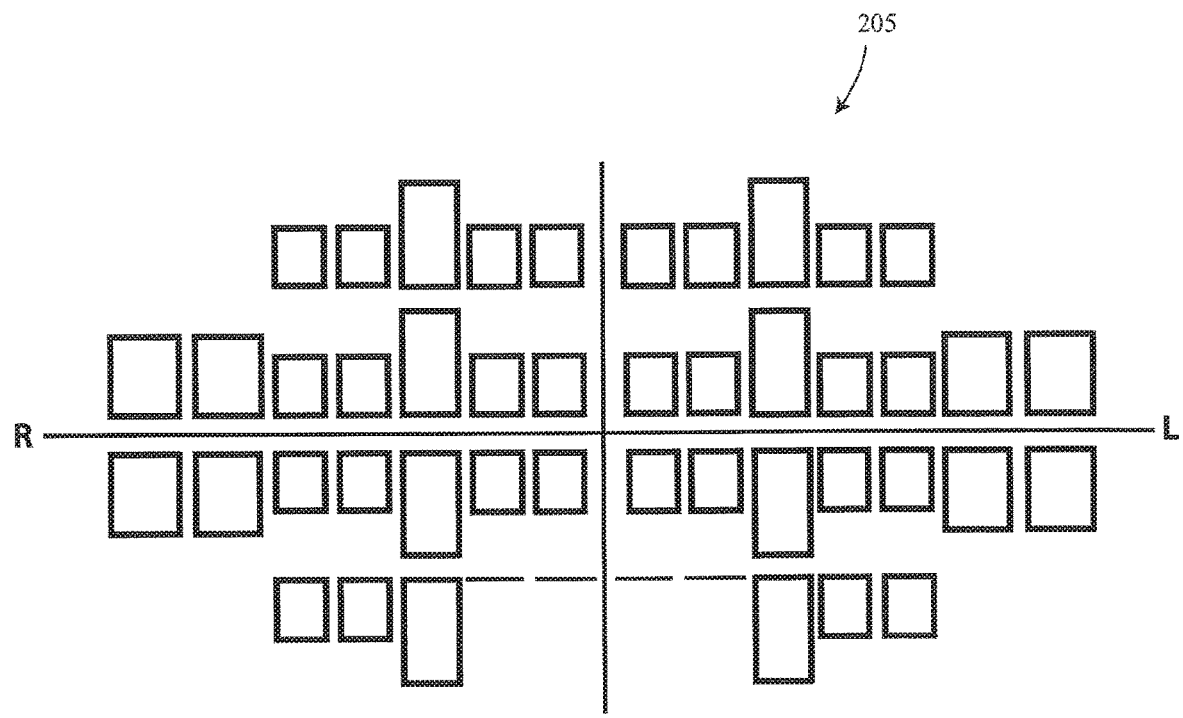
FIG. 4 illustrates a schematic diagram of another dentition chart in an embodiment of the present invention.

Further, the professional may examine the dentition of the patient and may indicate findings on a more detailed dentition chart 205 as shown in FIG. 4. For example, the professional may determine whether the teeth present may be only deciduous except for the first permanent molars. If so, the professional may determine whether the lower deciduous incisors may be straight with no crowding and no spacing. The professional may also determine whether any permanent teeth may be present. If so, the professional may examine the patient and indicate them on the dentition chart 205.

The professional may also determine whether the upper central incisors and/or the lateral permanent incisors, if present, may be lingually inclined. The professional also may determine whether the tips of the upper canines and the lower canines may be in an improper position. If so, the professional may indicate where the improper canine tip should be positioned. The professional may determine whether any permanent or deciduous teeth may be crooked and/or missing and if there may be enough room for them. The professional may indicate the observations on the dentition chart 205. In a like manner to Program B, the professional may perform the decay check, an open-bite check, a Class III relation check, a cross-bite check, a habit check and/or a dentition check.

The system 10 may identify various landmarks after the professional may scan the dentition. The CPU 20 also may identify landmarks from a scanned study cast of dentition or the professional may personally identify the landmarks by hand. Using the wand 45 of the IC 40 to scan the mouth of the patient may provide a digitized dentition that may be more reliable, consistent and unbiased. The following landmarks may be identified:

a) an upper incisal edge and/or a lower incisal edge of one central incisor that may be same tooth on the same side, b) mesial of the upper deciduous canines and/or the lower deciduous canines or permanent canines, if erupted;

c) mesial and distal of all four upper permanent incisors if all may be present, if not, use the permanent teeth that may be present in mouth and the four lower permanent incisors;

d) tip of the cusp of the upper canines and the lower canines if in proper position. If a canine may be in an improper position, mark the top in the proper position labially-lingually, not mesio-distally; and e) distal of the deciduous or permanent canines and distal of upper and lower of the deciduous molar or the mesial of first permanent molar if deciduous second molar may be missing or may have decay with a loss of space.

The CPU 20 may perform a lower arch length analysis. For example, the tip of the lower canine to the tip of other lower canine may be multiplied by a factor from the database according to the age of the patient may be the available space of lower incisor area. Also, the system 10 and/or the CPU 20 may measure the available space for the lower permanent incisors by multiplying the mesial-distal width of lower central by four and adding one. Also, the widths of all four lower permanent incisors may be measured, if all may be present. Depending on the age of the patient, the CPU 20 may access the database 55 to predict future crowding, future risks and treatment recommendations. For example, the information specific to the age of the patient may be presented to parent.

The CPU 20 may access the database 55 for information on mandibular treatment possibilities to determine what crowding severities may be appropriate for treatment and the associated fees that may be charged. The information may be based upon which teeth are present. The information may provide multiple treatment possibilities, such as, only using the Occlus-o-Guide® appliance; using the Occlus-o-Guide® appliance with stripping both deciduous lower second molars; and using the Occlus-o-Guide® appliance with stripping the deciduous first lower molar and/or the second lower molar and using a bumper. The information from the database 55 may also indicate the point at which the case may be too severe and may recommend a fixed orthodontic appliance treatment procedure. Further information in the database 55 may provide treatment options when certain upper permanent incisors may be present. Moreover, information in the database 55 may provide treatment options if both second deciduous molars may be present; if only one second deciduous molar may be present; and if both second deciduous molars may be missing and the leeway space may have already closed. Such a case may require an Ortho-T® appliance adult dentition case.

Most cases may be determined diagnostically on whether to treat by the crowding of the lower arch and if there may be sufficient room for successful treatment. However, in some cases in which the upper may be the determiner, the lower arch length analysis may be done by the CPU 20 first. If the case may be an acceptable case, the CPU 20 may determine if the upper arch length analysis and/or the result may be acceptable or not. If either the lower or upper arch length analysis may indicate that the case may be an unacceptable one, the professional may recommend a fixed orthodontic appliance treatment procedure. The orthodontist may recommend fixed orthodontics.

The CPU 20 may perform an upper arch-length analysis for the incisal area. The first procedure may be to measure the tip of the upper canine to the tip of the other canine and multiply this measurement by a factor of 0.9932 to determine the upper available space. The upper canines may be required to be in the proper position for an available space measurement. If the canine tip may be in an abnormal position, the professional may enter the proper position of the canine in the CPU 20 using the UI 30. To obtain the upper required space, several options may be available depending on the presence or absence of the upper permanent incisors. An upper permanent incisor may preferably be used to obtain the required space if the tooth may be available to measure. For example, the width of upper permanent central incisor may be multiplied by a factor of 3.5212 to obtain the upper required space. Also, the sum of the widths of all four upper permanent incisors may be used to obtain the upper required space. Further, if no upper permanent incisors may be present, the width of the lower permanent central incisor may be multiplied by a factor of 5.6776. The required space may be subtracted from the available space to obtain the required space.

The amount of crowding that may be corrected may depend on whether the upper deciduous second molars may be present, if one may be present, or neither may be present with the leeway space closed. When both deciduous upper molars may not be present, the case may be diagnosed as an adult dentition in Program D for patients of twelve years of age to eighteen years of age. The CPU 20 may access information in the database 55 to indicate the upper crowding severity that may be corrected when both deciduous upper molars may be present.

The CPU 20 may access information in the database 55 regarding the amounts of correction possible with both deciduous upper molars and with only one upper deciduous molar present. The information may provide the amounts that may not be corrected. If the upper permanent incisors and/or the lower permanent incisors may be lingually-inclined, the appliance may tip the teeth forward to increase the crowding correction by one mm to two mm. The amount of correction may depend on whether one upper second deciduous molar and/or two upper second deciduous molars may be present in cases with lingually inclined upper incisors. The information may be presented to the parent of the patient. The database 55 may also provide information regarding the amounts of correction possible with both deciduous upper molars and/or with only one upper deciduous molar present. The information may provide the amounts that may not be corrected. The treatment may be with or without an additional appliance like a bumper.

If all four or less upper permanent incisors are fully erupted, all four upper permanent incisors and/or the erupted upper permanent incisors may be measured. The upper required space may be the total mesial-distal widths of the four upper permanent incisors. If any or part of the upper permanent incisors may be in place, the required space may be determined by the dimensions of the upper permanent incisors rather than the width of the lower permanent central incisor.

The system 10 may also calculate other dental conditions. In an embodiment, the CPU 20 may compare measurements with information in the database 55. For example, FIGS. 13-16 illustrate information related to crowding, overbite and overjet. For example, overbite may be determined. The CPU 20 may measure the overbite described in Program B. The CPU 20 may access information in the database 55 to obtain the parameters to estimate future problems for the overbite and/or to recommend treatment. The information may be given to the parent as in Program B.

An open-bite, if present, may be measured according to Program B. If the open-bite may be skeletal, the case may be not acceptable and may be referred for fixed orthodontic treatment and/or surgery. The CPU 20 may access the database 55 for information that may indicate at what age various severities of open-bite may be appropriate for correction. Generally, open-bites caused by current or previous habits, such as thumb-sucking and/or improper swallowing may not be recommended for treatment for patients over ten years of age. Any patient with an open-bite with an N-Me distance exceeding two S.D. may be not a candidate for treatment.

Overjet may be measured according to Program B. The CPU 20 may access information in the database 55 to determine whether treatment may be recommended according to the age of a patient. The incidence of overjet, together with the other factors, may be presented to the parent in a letter with the data for the patient. The data for treatment time and retention time may be found in the information from the database 55.

Class III and Pseudo Class III malocclusions may be measured according to Program B. Treatment for any cross-bite may be indicated for patients from seven years of age to twelve years of age. Pseudo Class III type cross-bites may be easily correctible from seven years of age to twelve years of age. Skeletal Class III problems may be determined as in Program B. Generally, any skeletal Class III problem not exceeding three mm may be minimized and/or may be prevented from becoming more severe with a Youth Class III appliance, for example.

Cross-bites may be observed by the professional as in Program B. The CPU 20 may access information in the database 55 to determine if the maxillary arch width may be considered abnormally narrow. If the maxillary arch width may be expanded, particularly if there may be a cross-bite and/or upper respiratory breathing problems, treatment may be recommended.

TMJ problems may be identified as in Program B. The same treatment recommendations may exist for the patient of seven years of age to twelve years of age as for younger patients. Information from the database 55 corresponding to the age of the patient may be used for estimations of treatment recommendations to present to the parent. TMJ problems may be corrected with removable appliances as long as an overjet and overbite exist. When the patient opens and closes from an end-to end position, the symptoms such as clicking and difficulty in opening may disappear. If so, the appliance may be used. If not, the patient may be referred to a TMJ specialist. Most cases may be treated with a removable appliance such as the Nite-Guide® appliance and Occlus-o-Guide® appliance.

Habits such as thumb sucking and/or finger sucking may be corrected. However, abnormal swallowing may be difficult to correct for a patient older than ten years of age and may be referred for orthodontic treatment by a specialist. Sleep problems may be outlined as in Program B.

The CPU 20 may present the findings to the parent of the patient in the initial letter together with the document of the initial diagnostic findings of the system 10. An example of the document of the findings may be similar to that shown in FIG. 6. The document may summarize the various problems a child may have, namely crowding, overbite, overjet, cross-bite, TMJ, habits and suspected sleep-disordered breathing problems and a narrow upper arch.

The CPU 20 may print out the document outlining these various eight elements of the dentition of the patient that may be from seven years of age to twelve years of age for the initial assessment. The full records assessment may be conducted to determine problems beyond the initial exam. For example, missing teeth, various impactions, and improper eruption paths of the incoming permanent teeth and/or the like may warrant a contradiction for the early mixed dentition therapy.

In an embodiment, the system 10 and/or the method 100 may also encompass the full records assessment of Program C as shown in step 135 of FIG. 2. As part of the full records assessment, the professional may take x-rays of the patient. For example, the x-rays may contain a digital panoramic x-ray film of the patient, a lateral digital cephalometric x-ray film, and/or one 3-D x-ray film. The 3-D x-ray film may be preferred since details may be clearer to see in such an x-ray. The imaging in the full records assessment may contain intra-oral and/or facial photographs. The professional may analyze the panoramic film and/or the 3-D film, if available, as part of the full records assessment. The panoramic film and/or the 3-D film may be analyzed by the system 10 and/or the method 100. For example, the CPU 20 may analyze the panoramic film and/or the 3-D film to ensure that all unerupted teeth may be present. The professional may also perform this review. If any permanent teeth may be missing, the missing teeth may be charted. The relative placement of the dentition may be organized on the dentition chart 205 as shown on FIG. 4. The erupted teeth may be indicated on the dentition chart 205. The professional may also take a hand and wrist x-ray film of the left hand for assistance in determining skeletal age of the patient.

The professional may perform an oral examination of the patient as part of the full records assessment. The professional may check the freeway space. The CPU 20 may also measure the freeway space by using two images of the face. The CPU 20 may analyze the panoramic film and/or the 3-D film to make determine whether all unerupted teeth may be present. The professional may perform this task. Further, the professional may check the unerupted teeth to determine whether the teeth may be erupting in the right position.

The professional may determine any rotations. The system 10 may measure certain areas of the nasopharynx and oropharynx. The CPU 20 may access the database 55 to determine whether the measurements may have any abnormalities. The professional may not any root resorption and/or may check the size of the adenoids. The professional may enter the information into the system 10 using the UI 30. The system 10 may determine the skeletal age of the patient and may be used to time any treatment required to occur at various ages including the start of the pubertal spurt. For example, the CPU 20 may access data, such as the information shown in FIGS. 7-9. Further, the professional may follow the same format of the examination as in Program B.

In addition, the CPU 20 may use the mesial-distal widths of the upper incisors and/or the lower incisors and may divide the upper total by the lower total to obtain a ratio. The ratio may indicate if the upper incisors and the lower incisors may be coordinated to provide an ideal occlusion of the front teeth following correction. An acceptable ratio of the lower incisors to upper incisors for a male patient may be 73.735% and may be 74.1762% for a female patient. The standard Bolton analysis for the male patient which may total the six anterior teeth divided into the widths of the six lower anterior teeth may be 78.4339% for the male patient and may be 78.125% for the female patient.

The system 10 may provide the document to the parent and/or the patient that may indicate problems noted initially and during the record assessments. The document may have information from the films, the skeletal age of the patient, the predicted adult height and/or the growth in height each year to full maturity.

Figure 10:
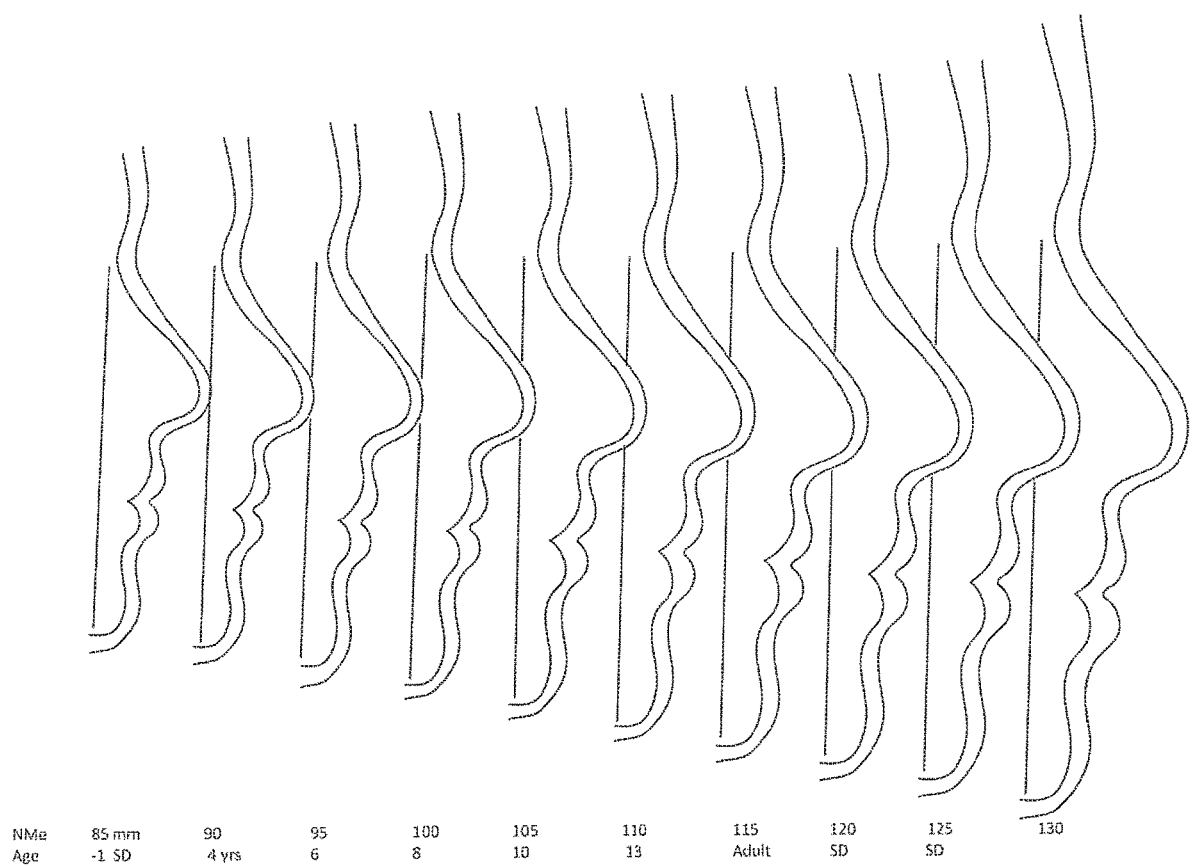
FIG. 10 illustrates a chart for use in an embodiment of a method in accordance with the present invention.

Also, the profile analysis with the profile of the patient superimposed over profile templates, such as the profile template illustrated in FIG. 10 for a female patient. A profile template corresponding to a male patient may also be provided and/or used, as desired. The document may have sample pictures of other similar cases with such problems as crowding, excessive overbites, overjets, open bites and the like that may show what the various problems may look like at twelve years of age if no treatment is initiated.

An appliance may be recommended for the patient. The size of the appliance may be calculated by the CPU 20 with access to the database 55. The system 10 may also provide the document that may explain the initial data as well as any data learned from the x-ray records.

As shown in FIG. 2, step 140 illustrates Program D of the method 100. Program D may be designed for children and/or patients ranging from twelve years of age to eighteen years of age. Program D may be configured to relate to the dentition and/or oral development of patients in this range. In particular, patients in this age range may have early permanent dentition. Thus, Program D may correlate the initial assessment and/or examinations of the patient to the specific age of the patient. The correlated initial assessment may focus the initial assessment on the current state of development of the patient. Certain assessments may not be indicated for the age range in Program D. However, other assessments may be critical at the current state of development of the patient. To this end, Program D may be performed as set forth hereinafter.

The system 10 and/or the method 100 may have the initial examination and/or assessment. The full records assessment may also be required. The patient may undergo the initial examination by the professional. The system 10 and/or the method 100 may generate a preliminary and/or initial assessment and/or diagnosis based upon the initial examination of the patient. The system 10 and/or the method 100 may provide such an assessment and/or diagnosis prior to the full records assessment.

In an embodiment, any one of the following problems may require a treatment recommendation and/or the full records assessment shown in step 145 of FIG. 2. The problems may be as follows:

1. Crowding/spacing in which a lower arch and an upper arch length analysis may be performed to determine whether the patient may be a candidate for treatment. Other problems, such as, for example, displaced teeth with space shortage, missing teeth and various other problems may be examined and noted by the professional.

2. Overbite greater than one and one quarter mm and/or an open bite of any severity 3. Overjet greater than one and one quarter mm and/or a Class III relation of any severity including zero mm which may be an end-to-end or pseudo Class III relation 4. Cross-bites of any severity 5. TMJ having any two symptoms except for limited opening 6. Habits such as, for example, thumb sucking, swallowing, speech problems and/or mouth breathing 7. Suspected sleep-disordered breathing problems 8. Narrow upper arch The system 10 and/or the method 100 CPU 20 may generate the document for the patient. The document may summarize whether any of the above eight items may be problems that may be considered beyond normal. The document may also explain why the full records assessment and/or probable treatment may be recommended. The document may contain the treatment time required, the patient responsibility, any fee involved, probabilities of success, any possible relapse and pictures what the teeth may look like without performing any treatment.

The CPU 20 may generate and/or print the document to the parent of the patient with findings for the parent to consider and/or study as shown in FIG. 6. The document may be generated after the initial examination.

The professional may examine the patient and enter the information on the UI 30 which may display the information on the monitor 35. For example, the examination may determine which teeth may be present and/or may be missing and may be indicated on the dentition chart 205. The examination may determine whether sufficient room for the tooth or teeth exists and/or whether crowding may be present. Further, the examination may determine whether the upper centrals and/or laterals may be lingually inclined; whether the canine tips may be in an improper position; and whether any teeth may be rotated and/or out of alignment. The examination may provide a decay check, if needed, as found in program B. Moreover, the examination may determine if the patient may have an open-bite, an excessively long face and/or a Class III problem. The examination may have the same TMJ check and/or habit check as in Program B.

Any lower crowding may be determined by an arch length analysis of the lower arch. The sum of the widths of the four or six lower front teeth may equal the required space. The available space may be the circumference around the lower arch along the incisal edges of the lower four anterior teeth or six anterior teeth. The distance either from the mesial of one canine to the other canine for an arch length analysis of only the incisors, or if the canines may be included, the distance may be from the distal of one canine to the distal of the other canine. If the crowding may be only in the incisal area, the shorter distance may be used between the canines. If the canines may be also crowded, the arch length analysis would include the canines. In either case the measurement may be the available space of the lower arch.

The required space may be subtracted from the available space to obtain the shortage, excess or normal arch. The crowding and/or spacing may be compared to information from the database 55 depending on the age of the patient. The information may be presented to the patient or the parent of the patient.

The upper arch length analysis may be done in the same manner. Treatment for an arch shortage in the upper arch of one half mm may be optionally recommended. Treatment for crowding of one mm or more may be recommended for a patient from twelve years of age to eighteen years of age. The treatment possibilities for crowding and/or spacing for the upper arch and/or the lower arch may be provided in the information in the database 55.

An analysis may be performed to determine if the upper incisors and the lower incisors may be coordinated to produce an ideal incisal occlusion as in Program C. If the coordination ratio indicates one arch may be different from the other, such as the upper may be smaller due to smaller upper laterals, the width estimate of the laterals may be obtained from the information in the database 55. A composite may be added to the smaller laterals to make the laterals a normal size.

Further, anterior spacing may be corrected. If there may be no overjet or a minimum overjet of up to two mm or three mm, the patient may require some bonding. If there may be an overjet of four mm or more, the spaces may typically be closed by using the Ortho-T® appliance. Also, overbites of any severity may be corrected provided sufficient vertical growth (ANS-Me) may remain. Typically, one mm of lower face height growth may be required to stabilize every mm of overbite correction. The database 55 may provide information as to what severity of overbite may be successfully corrected with minimal relapse as well as the amount of relapse that may be expected according to the age of the patient. A more accurate estimate may result if the skeletal age of the patient may be used instead of chronological age. The information may indicate how much vertical growth ANS-Me may be needed for successful overbite correction without future relapse. The information may also indicate the amount of expected relapse that may occur typically in a treated overbite.

Open-bites at twelve years of age and over may be difficult to treat successfully. Therefore, such patients may be referred for fixed orthodontic treatment or surgery, as appropriate. Overjet according to the severity and the age of the patient may be estimated from the information in the database 55. Also, the information may indicate which overjets may be appropriate for treatment and the amount of relapse that may be avoided. Mandibular prognathism such as Class III and pseudo Class III occlusions may be indicated in the initial examination. Generally, skeletal Class III malocclusions may not be appropriate cases after twelve years of age; however, minor Class III cases of less than three mm may be helped by a Class III appliance that may be capable of improving or at least minimizing the severity of the problem. Pseudo Class III end-to-end occlusions may be corrected with the Ortho-T® appliance.

Cross-bites may be correctable as long as space exists or may be provided, for example, with a bumper for proper correction. TMJ problems may be treatable with the exception of closed-lock and/or limited opening problems. Information from the database 55 may indicate if growth remains to advance the mandible sufficiently to accommodate the forward advancements of the mandible. Also, the information may indicate the growth remaining to accommodate vertical changes. For example, if the mandible may be advanced three mm and opened three mm to correct the clicking and opening deviation, then three mm of horizontal and vertical growth may be required to obtain a permanent result. This amount of growth may be obtained anytime up to fifteen years of age in a male patient and anytime up through twelve years of age in a female patient for this vertical amount of three mm. The horizontal growth on the other hand may be achieved anytime up through seventeen years of age in the male patient and anytime up through fourteen years in the female patient. If these amounts may be not achievable, such as in the case of a patient of eighteen years of age, the appliance may be required indefinitely as a retainer. For example, the Ortho-T® appliance may be worn as a retainer one night per week to prevent symptoms from returning in the future.

Habits such as thumb-sucking may be corrected at any age. Mouth-breathing may be more easily corrected at younger ages of ten years of age and younger; however, after the patient may have reached twelve years of age, the habits may also be possible to correct. Tonsil and adenoid enlargement may be a frequent cause of mouth breathing. Thus, removal of the tonsil and/or the adenoid followed by using the Ortho-T® appliance may be a successful treatment. Tongue-thrust swallowing problems may be difficult to successfully treat in patients older than ten years of age and may be a contraindication for this form of treatment at twelve years of age or older.

Sleep-disordered breathing not caused by apnea or hypopnea may be successfully treated by either enlargement of the upper arch and/or by advancing the mandible and tongue with a Habit-Corrector® appliance (a registered trademark of Ortho-Tain, Inc.) and/or the Ortho-T® appliance. The upper arch enlargement may improve the opening of the nasopharynx, while mandibular advancement may improve the narrow oropharynx.

Narrowed upper arch widths may be analyzed. Upper arches that may be excessively narrow that exceed the abnormal limits may be also accompanied by breathing problems, particularly those with nasopharyngeal narrowing. The full records assessment with the cephalometric x-ray and/or the 3-D film may indicate treatment may be treated with upper arch expansion.

The CPU 20 may provide the document to the parent summarizing the findings in the initial examination regarding the eight various elements of the dentition of the patient. The patient may require the full records assessment with the three x-ray films to verify if treatment may be recommended. Also, a skeletal age determination and a prediction of the start of the pubertal growth spurt may be performed.

In an embodiment, the system 10 and/or the method 100 may also encompass the full records assessment of Program D as shown in step 145 of FIG. 2. As part of the full records assessment, the professional may take x-rays of the patient. For example, the x-rays may contain a digital panoramic x-ray film of the patient, a lateral digital cephalometric x-ray film, and/or one 3-D x-ray film. The 3-D x-ray film may be preferred since details may be clearer to see in such an x-ray. The imaging in the full records assessment may contain intra-oral and/or facial photographs. The professional may analyze the panoramic film and/or the 3-D film, if available, as part of the full records assessment. The panoramic film and/or the 3-D film may be analyzed by the system 10 and/or the method 100. For example, the CPU 20 may analyze the panoramic film and/or the 3-D film to ensure that all unerupted teeth may be present. The professional may also perform this review. If any permanent teeth may be missing, the missing teeth may be charted. The relative placement of the dentition may be organized on the dentition chart 205 as shown on FIG. 4. The erupted teeth may be indicated on the dentition chart 205.

The professional may take a hand and wrist x-ray film of the left hand as in Program C to assist in determining skeletal age of the patient. The oral examination may involve a check of the freeway space. The professional may either mark a point on the nose and the bottom of the chin and may hand measure the distance at rest and again at occlusion. The CPU 20 may also measure the distance and may take two photographs of the face of the patient. The CPU 20 may also measure the A, B, ANS, Menton, gnathion, articulare, porion, orbitale, PNS and the long axis of upper central incisors and the lower central incisors. Also, various measurements may be made of the size of airway at two distances from the uvula to the posterior wall of the nasopharynx and from the base of the tongue to the posterior wall of the oropharynx. The CPU 20 may compare the measurements to norms for normal and abnormal amounts and may indicate if the airway may be normal or abnormal. The CPU 20 may access information in the database 55 to determine whether to treat and/or the reason or reasons to treat. The CPU 20 may perform standard cephalometric analyses as the professional desires. Such analyses may include the Northwestern Reidel, Downs, Steiner, Sassouni, Harvold, Wits, Rickets, McNamara and/or the like.

The overbite and overjet may be measured, and treatment may be recommended according to information from the database 55. In an embodiment, the CPU 20 may compare the obtained measurements with information in the database 55. For example, FIGS. 17 and 18 illustrate information related to overbite. Further, FIGS. 19-21 illustrate information related to crowding, overbite and overjet, respectively. The adenoid tissue may be examined for swelling. If the adenoid tissue may be significantly swollen, the patient may be referred to a specialist for surgical removal.

The professional may estimate if the upper canine angulation may be normal or abnormal. If the angulation may be excessively abnormal, the professional may recommend a fixed orthodontic appliance treatment procedure. The presence of other impactions not correctable with the use of a bumper may require an orthodontist and/or fixed treatment.

The professional may estimate the skeletal age of the patient which may be used rather than the chronological age of the patient. The use of the skeletal age may yield greater accuracy when using information from the database 55. Any recommended interceptive treatment that may be within a year prior to the beginning of the pubertal growth spurt should be delayed to the start of the spurt. The information may provide overbite and overjet timing that may yield successful treatment with minimal relapse due to lack of vertical or horizontal growth from six years of age to eighteen years of age.

Suspected sleep problems for patients of twelve years of age to eighteen years of age may result from suspected swollen tonsils and/or adenoids. Abnormal swelling may be referred to a pediatrician. If the patient snores three nights per week to seven nights per week, the patient may wear the Ortho-T® appliance to keep the mandible and the tongue from drifting posteriorly while sleeping. Any patient suspected of having apnea or hypopnea may have a home night sleep study or referred to a sleep specialist.

If the patient may be mouth breather, the professional may check if the patient may easily breathe through the nose. If in question, the professional may refer the patient to a pediatrician for a breathing analysis and/or the home night sleep study. If the patient has a deviated septum, polyps and/or the like, the professional may refer the patient to the ENT specialist. If the patient may easily breathe through the nose, the professional may issue the patient the Ortho-T® appliance for night use and two hours of daily use if the patient may be a daytime mouth breather. Narrowed upper arch widths may be analyzed. A rapid palatal expander may not be used or may be used with daily checks on expansion any time after end of the pubertal spurt or even one year prior to the end of the spurt as shown in FIGS. 7-9.

The profile of the patient may be oriented on the profile template analysis shown in FIG. 10 with the appropriate template according to the N-Me distance of the patient. The areas of the profile that may be abnormal, such as recessive lips, protrusive nose, receding chin, long vertical face, short upper lip, long chin and the like may allow them to fall outside of template margins. The normal profile characteristics may be kept within the template margins, such as the forehead and the upper part of the nose. The CPU 20 may provide a visual tracing of the profile of the patient within the template that shows what ideally may be corrected. The proper treatment, such as advancement of the mandible, retraction of protrusive teeth, lengthening of the face and/or the like may be recommended. The treatments may be watched with a subsequent profile check on the template to verify if the treatment goals may be achieved.

The professional may determine the skeletal age of the patient and may use the chronological age of the patient. The CPU 20 may calculate the predicted height of the patient using information the database 55 and may predict the growth in height expected each year from the information. Percentage increases in height may be used for each following year. The percentage multiplied by the predicted height may give the height increase for each year until maturity.

Further, the CPU 20 may provide pictures that may represent the problem and/or how the problem may appear in the future if nothing may be done to correct the problem. The pictures may be printed with pictures of the patient and may be issued to the parent with the final letter to the parent with data similar to FIG. 6.

The CPU 20 may compare the initial diagnosis for treatment and/or may indicate if any problems from the final records assessment. The comparison may indicate that treatment with a bumper and the Occlus-o-Guide® appliance may be ineffective due to multiple missing teeth, improper angulation of upper canines, impacted teeth and/or the like. If so, the professional may refuse treatment and may recommend a fixed orthodontic appliance treatment procedure.

As shown in FIG. 2, step 150 illustrates Program E of the method 100. Program E may be designed for patients ranging from eighteen years of age to adulthood. Program E may be configured to relate to the dentition and/or oral development of patients in this range. In particular, patients in this age range may have mature permanent dentition. Thus, Program E may correlate the initial assessment and/or examinations of the patient to the specific age of the patient. The correlated initial assessment may focus the initial assessment on the current state of development of the patient. Certain assessments may not be indicated for the age range in Program E. However, other assessments may be critical at the current state of development of the patient. To this end, Program E may be performed as set forth hereinafter.

The system 10 and/or the method 100 may have the initial examination and/or assessment. The full records assessment may also be required. The patient may undergo the initial examination by the professional. The system 10 and/or the method 100 may generate the preliminary and/or initial assessment and/or diagnosis based upon the initial examination of the patient. The system 10 and/or the method 100 may provide such an assessment and/or diagnosis prior to the full records assessment.

In an embodiment, any one of the following problems may be require a treatment recommendation and/or the full records assessment shown in step 155 of FIG. 2. The problems may be as follows:

1. Crowding/spacing in which a lower arch and an upper arch length analysis may be performed to determine whether the patient may be a candidate for treatment. Other problems, such as, for example, displaced teeth with space shortage, missing teeth and various other problems may be examined and noted by the professional.

2. Overbite greater than 1.25 mm and/or an open bite of any severity

3. Overjet greater than 1.25 mm) and/or a Class III relation of any severity including zero mm which may be an end-to-end or pseudo Class III relation 4. Cross-bites of any severity 5. TMJ having any two symptoms except for limited opening 6. Habits such as, for example, thumb sucking, swallowing, speech problems and/or mouth breathing 7. Suspected sleep-disordered breathing problems 8. Narrow upper arch The system 10 and/or the method 100 CPU 20 may generate the document for the patient. The document may summarize whether any of the above eight items may be problems that may be considered beyond normal. The document may also explain why the full records assessment and/or probable treatment may be recommended. The document may contain the treatment time required, the patient responsibility, any fee involved, probabilities of success, any possible relapse and pictures what the teeth may look like without performing any treatment.

The CPU 20 may generate and/or print the document as shown in FIG. 6. The document may be provided to the parent of the patient with findings for the parent to consider and/or study. This document may be generated after the initial examination.

The professional may examine the patient and may enter the information using the UI 30. The information may display on the monitor 35. For example, the examination may determine which teeth may be present and may be indicated on the dentition chart 205. The same examination that may have been performed in Program D for the patient of twelve years of age to eighteen years of age may be done.

The professional may examine the patient and to classify the molars and may indicate the class on the dentition chart 205. The examination may determine whether the midline may be off. Further, the examination may determine whether the patient may have posterior spacing more than two mm.

Any lower crowding may be determined by an arch length analysis of the lower arch. The sum of the widths of the four or six lower front teeth may equal the required space. The available space may be the circumference around the lower arch along the incisal edges of the lower four anterior teeth or six anterior teeth. The distance either from the mesial of one canine to the other canine for an arch length analysis of only the incisors, or if the canines may be included, the distance may be from the distal of one canine to the distal of the other canine. If the crowding may be only in the incisal area, the shorter distance may be used between the canines. If the canines may be also crowded, the arch length analysis would include the canines. In either case the measurement may be the available space of the lower arch.

The required space may be subtracted from the available space to obtain the shortage, excess or normal arch. The crowding or spacing may be compared to information from the database 55 depending on the age of the patient. The information may be presented to the patient or the parent of the patient.

The upper arch length analysis may be done in the same way. Treatment for any arch shortage in the upper arch that may be one half mm may be optionally recommended while crowding of one mm or more may be recommended for a patient from twelve years of age to eighteen years of age. The treatment possibilities for crowding and spacing for the upper arch and/or the lower arch may be provided in the information in the database 55.

An analysis may be performed to determine if the upper incisors and the lower incisors may be coordinated to produce an ideal incisal occlusion as in Program C. If the coordination ratio indicates one arch may be different from the other, such as the upper may be smaller due to smaller upper laterals, the width estimate of the laterals may be obtained from the information in the database 55. A composite may be added to the smaller laterals to make the laterals a normal size.

Further, anterior spacing may be corrected. If there may be no overjet or a minimum overjet of up to two mm or three mm, the patient may require some bonding. If there may be an overjet of four mm or more, the spaces may typically be closed by using the Ortho-T® appliance.

Overbites that may be successfully corrected from eighteen years of age onward into adulthood may not depend on vertical facial growth since there may be no growth remaining. Overbites of about four mm may be corrected, but about fifty percent may relapse. However, correction may be recommended if there may be a TMJ problem. Therefore, if a patient has an overbite problem that may exceed four mm or five mm, the patient may be informed that the overbite may not successfully correct and/or may relapse. Overjet may have the same restrictions as overbite and may experience the same relapse as the overbite.

Open-bites and Class III malocclusions may be contraindicated and may not be recommended for this form of treatment and may be referred for fixed orthodontics or surgery. Fixed orthodontics may involve reverse head-gear or extraction of a lower incisor or premolars. Mandibular set-back surgery in Class III cases exceeding three mm may be recommended. Open-bites treated orthodontically may be a problem and may involve myofunctional therapy which may result in significant open-bite closure prior to any start of fixed orthodontics and/or surgical correction.

TMJ problems may be minimized with mandibular advancement and/or overbite reduction and may also involve posterior teeth eruption. If this eruption does not take place within two years, forceful eruption with fixed appliances may be required. Lifetime retention may be required, such as nighttime wear one night per week with the same Ortho-T® appliance used for correction.

Habits such as thumb sucking may be corrected, often with a few sessions of a fixed anti-sucking device. Mouth breathing may also be helped, particularly at younger ages. Swallowing habits may be most difficult and may be a contraindication at these late ages.

Sleep-disordered breathing may be strongly associated with apnea, hypopnea, and snoring. The patient may require a night-home sleep study. If apnea and hypopnea may be ruled out, a cephalometric analysis may be recommended.

Narrowed upper arch widths may be analyzed. Upper arches that may be excessively narrow that may exceed the abnormal limits may be accompanied by breathing problems. If the patient may be a mouth breather and/or has difficulty breathing through the nose, treatment may be recommended. However, rapid palatal expansion should not be used at this age.

The CPU 20 may provide the document to the parent summarizing the findings in the initial examination similar to the data presentation of FIG. 6. The patient may require the full records assessment with the three x-ray films to verify if treatment may be recommended.

In an embodiment, the system 10 and/or the method 100 may also encompass the full records assessment of Program E as shown in step 155 of FIG. 2. As part of the full records assessment, the professional may take x-rays of the patient. For example, the x-rays may contain a digital panoramic x-ray film of the patient, a lateral digital cephalometric x-ray film, and/or one 3-D x-ray film. The 3-D x-ray film may be preferred since details may be clearer to see in such an x-ray. The imaging in the full records assessment may contain intra-oral and/or facial photographs. The professional may analyze the panoramic film and/or the 3-D film, if available, as part of the full records assessment. The panoramic film and/or the 3-D film may be analyzed by the system 10 and/or the method 100. For example, the CPU 20 may analyze the panoramic film and/or the 3-D film to ensure that all unerupted teeth may be present. The professional may also perform this review. If any permanent teeth may be missing, the missing teeth may be charted. The relative placement of the dentition may be organized on the dentition chart 205 as shown on FIG. 4. The erupted teeth may be indicated on the dentition chart 205.

The professional may perform an oral examination of the patient as part of the full records assessment. The oral examination may be the same as described in Program D. An appliance may be recommended for the patient. The size of the appliance may be calculated by the CPU 20 by accessing information in the database 55. The system 10 may also provide the document that may explain the initial data as well as any data learned from the x-ray records.

In an embodiment, an orthodontist may use the system 10. The CPU 20 may be programmed to correspond to his or her own preferences. For example, the orthodontist may indicate desired treatment parameters, such as a treatment range for overbite, overjet and crowding. The system 10 may provide data to the orthodontist for his or her personal treatment philosophy, such as when to extract teeth to provide space and when to expand the arches and/or the like. Also, various treatment possibilities, such as extraction of premolars, incisors, molars, Herbst appliance, Twin-Block, rapid palatal expander, quad-helix, Damon technique, Frankel, Bionator, Activator and the like may be programmed into the CPU 20. The orthodontist may indicate the severity and conditions under which such appliances may be recommended and/or used.

The CPU 20 may categorize results based upon recommendations that may be helpful and/or time saving for the orthodontist. Such treatment parameters may be programmed for each age group that the orthodontist may treat, such as the three age ranges, namely: a) mixed dentition for patients of eight years old to twelve years old, b) the early adult dentition for patients of twelve years old to eighteen years old and c) the late adult dentition. The orthodontist may also be interested in early deciduous dentition and transitional dentition.

In particular, the orthodontist may indicate which treatment possibilities may be important for correction for patients with mixed dentition, such as, crowding and/or spacing, overbite and/or open bite, overjet and/or Class III relation, cross-bites, TMJ disturbances, habits such as thumb sucking, swallowing, mouth breathing, speech problems, suspected sleep disordered breathing, narrow upper arch, canine impactions and/or other impactions, multiple missing teeth and/or ankylosed teeth, erratic eruption of posteriors and/or the like.

Further, embodiments of the system 10 and/or the method 100 may provide information and/or data to estimate sizes of appliances that are gauged on sizes of the dentition and/or the arches. Appliances available from any manufacturer may be estimated using the system 10 and/or the method 100. Moreover, various types of appliances may be fabricated from the data obtained by the system 10 and/or the method 100. The appliances may be fabricated using stereo lithography and/or other methods.

Also, embodiments of the system 10 and/or the method 100 may provide information and/or data to recommend sizes of bands to cement onto the teeth of the patient. The system 10 and/or the method 100 may provide information and/or data to determine proper angulations of brackets for the teeth of the patient. Moreover, embodiments of the system 10 and/or the method 100 may provide information and/or data to determine the skeletal age of the patient from the hand x-ray film and to predict future growth and/or to predict the timing of growth spurts.

Moreover, the present invention is not limited to the specific arrangement of the components illustrated in the figures. It should be understood that various changes and modifications to the presently preferred embodiments described herein will be apparent to those having ordinary skill in the art. Such changes and modifications may be made without departing from the spirit and scope of the present invention and without diminishing its attendant advantages. It is, therefore, intended that such changes and modifications be covered by the appended claims.

The invention claimed is:

1. A method comprising:
providing a plurality of diagnostic programs associated with characteristics of developing dentition of a patient;
performing an initial assessment of the patient corresponding to the developing dentition of the patient wherein the initial assessment uses an imaging device to locate points in a mouth of the patient wherein the imaging device generates imaging data;
transferring the imaging data to a central processing unit wherein the central processing unit obtains measurements associated with selected points in the mouth of the patient and predicts future orthodontic conditions of the patient based upon the measurements in view of the diagnostic programs stored on the central processing unit; and
providing a report of findings of the initial assessment to the patient and a doctor with treatment recommendations based upon the findings.

2. The method of claim 1 wherein the diagnostic program corresponds to characteristics of the developing dentition of the patient wherein the dentition has early deciduous dentition or erupting adult incisors.

3. The method of claim 1 wherein the diagnostic program corresponds to characteristics of the developing dentition of the patient wherein deciduous dentition is being replaced by permanent dentition.

4. The method of claim 1 wherein the diagnostic program corresponds to characteristics of the developing dentition of the patient wherein the adult incisors are fully erupted and further wherein the premolars and second permanent molars are erupted.

5. The method of claim 1 wherein the diagnostic program corresponds to characteristics of the developing dentition of the patient wherein adult teeth are erupted and a leeway space has closed or after all facial growth has stopped.

6. The method of claim 1 further comprising: programming the central processing unit to correspond to particular treatment parameters of an orthodontist.

7. The method of claim 1 further comprising: determining from the findings of the initial assessment whether the patient is a candidate for treatment without further assessment.

8. The method of claim 1 further comprising: repeating the initial assessment at a later date to determine development of problems indicating subsequent treatment or to alter a current treatment procedure.

9. The method of claim 1 further comprising: evaluating treatment progress of the patient and recommending different treatment options.

10. The method of claim 1 further comprising: providing a document having information from the initial assessment to the patient wherein the information is associated with the orthodontic conditions determined from the initial assessment and proposed treatments.

11. The method of claim 1 further comprising: performing a full records assessment following the initial assessment if indicated by the findings of the initial assessment wherein the full records assessment has x-rays of the patient.

12. A system comprising:
an imaging component configured to locate landmarks in a mouth of a patient wherein the imaging component locates the landmarks and generates imaging data of the landmarks; and
a central processing unit having access to a database with information associated with orthodontic conditions wherein the central processing unit receives the imaging data from the imaging component and generates measurements associated with landmarks and dentition in the mouth of the patient and further wherein the central processing unit predicts orthodontic conditions of the patient based upon the measurements and the information in the database and recommends treatments to the patient based upon the predicted orthodontic conditions with reference to diagnostic programs stored on the central processing unit.

13. The system of claim 12 further comprising: a display configured to show images of the predicted orthodontic conditions to the patient.

14. The system of claim 12 wherein the imaging component locates the points and generates imaging data of the points in the mouth without user input.

15. The system of claim 12 wherein the database has images of orthodontic conditions to provide to the patient.

16. The system of claim 12 wherein the central processing unit is programmed to correspond to a particular treatment philosophy of a user.

17. The system of claim 12 wherein the central processing unit generates information on incidence of the orthodontic condition and predictions of severity of the orthodontic condition by a certain age of the patient.

18. The system of claim 12 wherein the central processing unit provides images of untreated orthodontic conditions at future ages to provide to the patient.

19. The system of claim 12 further comprising: a document output component connected to the central processing unit wherein the document output component provides an output to the patient.

* * * * *